(12) United States Patent
Hueil et al.

(10) Patent No.: US 7,785,294 B2
(45) Date of Patent: Aug. 31, 2010

(54) WOVEN PROTECTOR FOR TROCAR SEAL ASSEMBLY

(75) Inventors: Geoffrey C. Hueil, Mason, OH (US); Michael S. Cropper, Edgewood, KY (US); Brian J. Thompson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1137 days.

(21) Appl. No.: 10/943,220

(22) Filed: Sep. 17, 2004

(65) Prior Publication Data

US 2005/0077689 A1    Apr. 14, 2005

Related U.S. Application Data

(60) Provisional application No. 60/506,782, filed on Sep. 30, 2003.

(51) Int. Cl.
*A61M 5/178*    (2006.01)
*A61B 17/34*    (2006.01)

(52) U.S. Cl. .................. 604/167.06; 606/185

(58) Field of Classification Search ............... 604/167, 604/115, 148, 164.01, 164.06, 170.02, 164.08, 604/164.11, 167.04, 164.12, 104, 107, 117, 604/256, 174, 264, 274, 278, 506, 167.01–167.06; 600/184; 606/108, 185, 190, 167, 182, 198; 251/149.1

See application file for complete search history.

(56) References Cited

U.S. PATENT DOCUMENTS

| | | | |
|---|---|---|---|
| 3,504,699 A | 4/1970 | Grise | |
| 3,773,233 A | 11/1973 | Souza | |
| 4,436,519 A | 3/1984 | O'Neill | |
| 4,601,710 A | 7/1986 | Moll | |
| 4,610,665 A | 9/1986 | Matsumoto et al. | |
| 4,654,030 A | 3/1987 | Moll | |
| 4,655,752 A * | 4/1987 | Honkanen et al. | ........... 604/256 |
| 4,902,280 A | 2/1990 | Lander | |
| 4,931,042 A | 6/1990 | Holmes et al. | |
| 4,932,633 A | 6/1990 | Johnson et al. | |
| 5,030,206 A | 7/1991 | Lander | |
| 5,053,013 A | 10/1991 | Ensminger et al. | |
| 5,104,383 A | 4/1992 | Shichman | |
| 5,203,773 A | 4/1993 | Green | |
| 5,209,737 A * | 5/1993 | Ritchart et al. | ......... 604/167.03 |
| 5,211,634 A | 5/1993 | Vaillancourt | |
| 5,246,425 A | 9/1993 | Hunsberger et al. | |
| 5,300,033 A | 4/1994 | Miller | |
| 5,308,336 A * | 5/1994 | Hart et al. | .............. 604/167.03 |
| 5,324,270 A | 6/1994 | Kayan et al. | |

(Continued)

FOREIGN PATENT DOCUMENTS

EP    0339945    11/1989

(Continued)

*Primary Examiner*—Kevin C Sirmons
*Assistant Examiner*—Andrew M Gilbert
(74) *Attorney, Agent, or Firm*—Welsh & Flaxman LLC

(57) ABSTRACT

A seal assembly for use in conjunction with a trocar assembly includes a seal body adapted for sealing about an instrument inserted through the trocar assembly. The seal assembly also includes a protector adjacent the seal body for protecting the seal body from instruments passing through the seal body. The protector comprises a plurality of protector segments woven together in a non-planar arrangement.

24 Claims, 15 Drawing Sheets

U.S. PATENT DOCUMENTS

| | | | |
|---|---|---|---|
| 5,342,315 A * | 8/1994 | Rowe et al. | 604/167.06 |
| 5,366,445 A * | 11/1994 | Haber et al. | 604/164.01 |
| 5,385,552 A * | 1/1995 | Haber et al. | 604/167.03 |
| 5,385,553 A | 1/1995 | Hart et al. | |
| 5,441,041 A | 8/1995 | Sauer et al. | |
| 5,456,284 A | 10/1995 | Ryan et al. | |
| 5,467,762 A | 11/1995 | Sauer et al. | |
| 5,534,009 A | 7/1996 | Lander | |
| 5,542,931 A | 8/1996 | Gravener et al. | |
| 5,569,160 A | 10/1996 | Sauer et al. | |
| 5,578,016 A | 11/1996 | Zinger | |
| 5,584,850 A | 12/1996 | Hart et al. | |
| 5,603,702 A * | 2/1997 | Smith et al. | 604/256 |
| 5,643,301 A | 7/1997 | Mollenauer | |
| 5,807,338 A | 9/1998 | Smith et al. | |
| 5,895,377 A | 4/1999 | Smith et al. | |
| 6,024,729 A | 2/2000 | Dehdashtian et al. | |
| 6,086,603 A | 7/2000 | Termin et al. | |
| 6,277,100 B1 | 8/2001 | Raulerson et al. | |
| 6,302,852 B1 | 10/2001 | Fleming, III et al. | |
| 6,352,520 B1 | 3/2002 | Miyazaki | |
| 6,569,120 B1 * | 5/2003 | Green et al. | 604/167.04 |
| 6,613,063 B1 | 9/2003 | Hunsberger | |
| 6,685,630 B2 | 2/2004 | Sauer et al. | |
| 6,702,787 B2 | 3/2004 | Racenet et al. | |
| 7,371,227 B2 * | 5/2008 | Zeiner | 604/167.03 |
| 7,481,795 B2 * | 1/2009 | Thompson et al. | 604/167.03 |
| 7,597,701 B2 * | 10/2009 | Hueil et al. | 606/185 |
| 2002/0007153 A1 | 1/2002 | Wells et al. | |
| 2002/0010425 A1 | 1/2002 | Guo et al. | |
| 2002/0072713 A1 * | 6/2002 | Almond et al. | 604/167.05 |
| 2004/0049173 A1 | 3/2004 | White et al. | |
| 2004/0064100 A1 | 4/2004 | Smith | |
| 2004/0147949 A1 | 7/2004 | Stellon et al. | |
| 2004/0215209 A1 * | 10/2004 | Almond et al. | 606/108 |
| 2004/0230161 A1 * | 11/2004 | Zeiner | 604/167.06 |
| 2007/0185453 A1 * | 8/2007 | Michael et al. | 604/164.01 |
| 2008/0161758 A1 * | 7/2008 | Insignares | 604/167.04 |

FOREIGN PATENT DOCUMENTS

| | | |
|---|---|---|
| EP | 0567142 | 10/1993 |
| EP | 0568383 | 11/1993 |
| EP | 0696459 | 2/1996 |
| WO | WO 94/03232 | 2/1994 |
| WO | WO 00/35529 | 6/2000 |
| WO | WO 2004/033004 | 4/2004 |

* cited by examiner

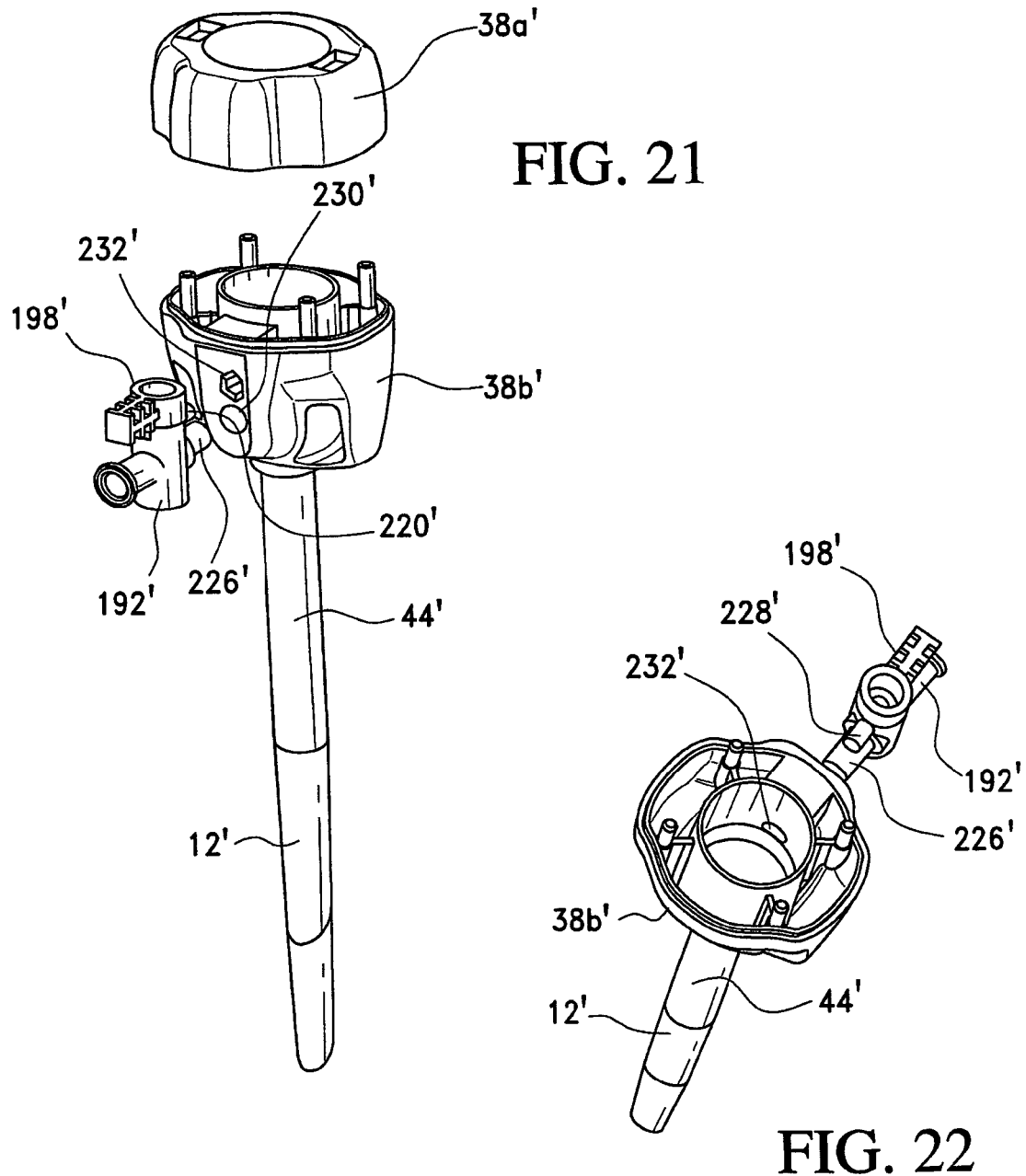

WOVEN PROTECTOR FOR TROCAR SEAL ASSEMBLY

CROSS REFERENCE TO RELATED APPLICATION

This application is based upon U.S. Provisional Patent Application No. 60/506,782, filed Sep. 30, 2003, entitled "WOVEN PROTECTOR FOR TROCAR SEAL ASSEMBLY", which is currently pending.

BACKGROUND OF THE INVENTION

1. Field of the Invention

The invention relates to protectors for use in conjunction with the sealing assemblies of trocars. More particularly, the invention relates to a woven protector for use in conjunction with a trocar sealing assembly.

2. Description of the Prior Art

A trocar assembly is a surgical instrument that is used to gain access to a body cavity. A trocar assembly generally comprises two major components, a trocar sleeve, composed of a trocar housing and a trocar cannula, and a trocar obturator. The trocar cannula, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar cannula is placed against the skin that has been previously cut with a scalpel. The trocar obturator is then used to penetrate the skin and access the body cavity. By applying pressure against the proximal end of the obturator, the point of the obturator is forced through the skin until it enters the body cavity. The trocar cannula is inserted through the perforation made by the obturator and the obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. An obturator, or other elongated surgical instruments or tools, axially extend into and are withdrawn from the trocar cannula through the proximal end portion of the chamber defined by the trocar housing.

It is common for a sealing arrangement or sealing device to be used in association with the trocar cannula and trocar housing to prevent the escape of fluid or gas during endoscopic procedures. During an endoscopic surgical procedure, the internal gas pressure must be maintained in order to successfully complete the procedure. In order to maintain the internal gas pressure while instruments are passed into and out of the trocar assemblies positioned in the abdominal cavity, sealing devices are required for both the obturators and instruments passing through the trocar cannula.

Seals must also offer good tear resistance, resistance to snagging and low friction with respect to associated seals and the insertion or removal of surgical instruments. Angular insertion of instruments relative to the central axis of the trocar cannula, instrument tip sharpness and end effecter geometry are driving factors in trocar seal failures. These three factors can cause "tenting" of the seal material. Once tenting occurs, continued distal motion of the penetrating instrument may result in seal tearing.

As such, a need exists for a protector capable of protecting the seal body as an obturator or instrument is passed through the trocar cannula. The present invention provides such a protector.

SUMMARY OF THE INVENTION

It is, therefore, an object of the present invention to provide a seal assembly for use in conjunction with a trocar assembly. The seal assembly includes a seal body adapted for sealing about an instrument inserted through the trocar assembly. The seal assembly also includes a protector adjacent the seal body for protecting the seal body from instruments passing through the seal body. The protector comprises a plurality of protector segments woven together in a non-planar arrangement.

It is also an object of the present invention to provide a trocar assembly with a trocar cannula having a proximal end and distal end and a trocar housing coupled to the proximal end of the trocar cannula for receiving and guiding an obturator through the trocar cannula. The trocar housing includes an open proximal end portion defining an opening provided with a proximal seal assembly and a distal seal assembly. The proximal seal assembly includes a seal body adapted for sealing about an instrument inserted through the trocar assembly and a protector adjacent the seal body for protecting the seal body from instruments passing through the seal body. The protector comprises a plurality of protector segments woven together in a non-planar arrangement.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 21 is an exploded view in accordance with an alternate embodiment of the trocar sleeve.

FIG. 22 is a partial exploded view in accordance with an alternate embodiment of the trocar sleeve as shown in FIG. 19.

DESCRIPTION OF THE PREFERRED EMBODIMENTS

Figure 1:
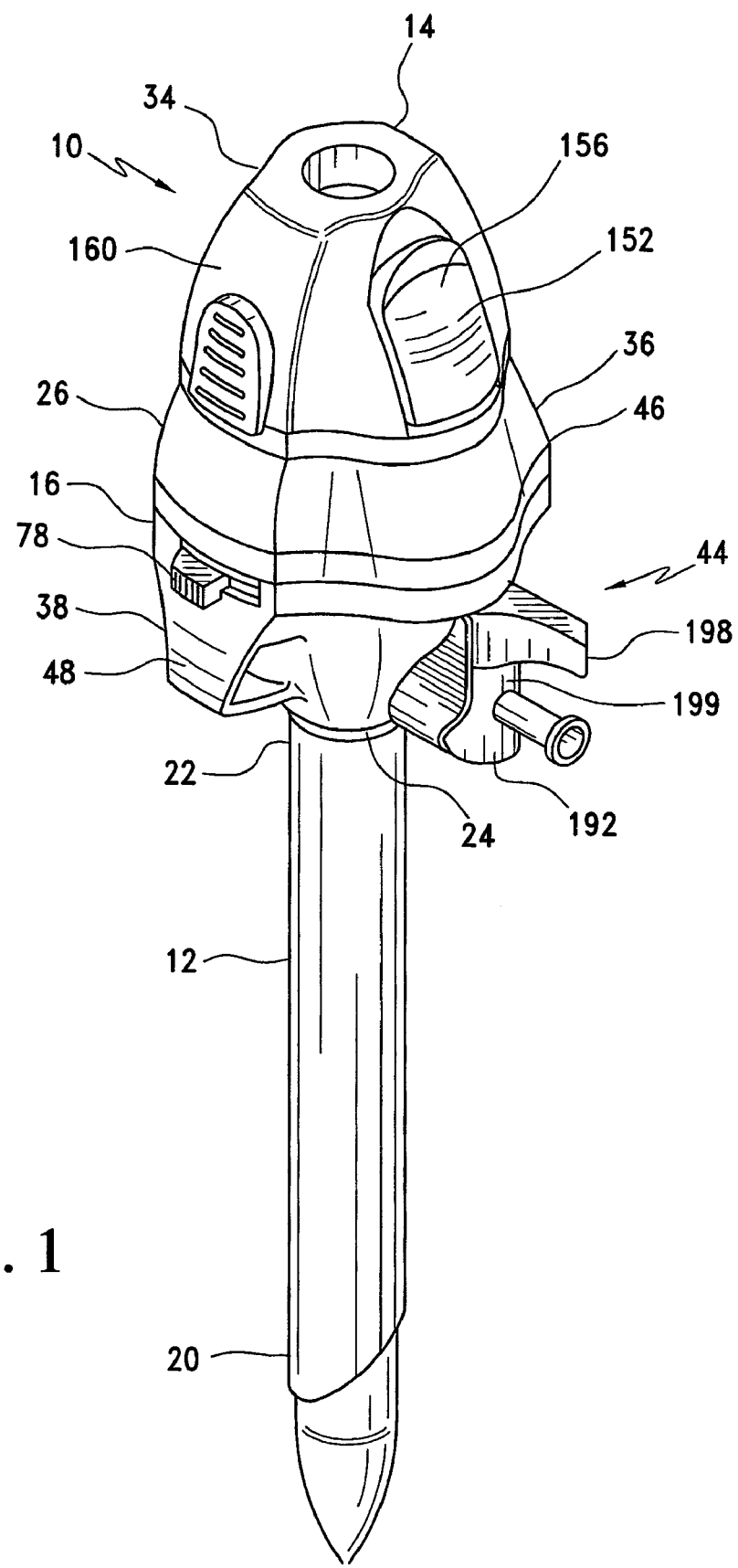
FIG. 1 is a perspective view of a trocar assembly in accordance with the present invention.
Figure 2:
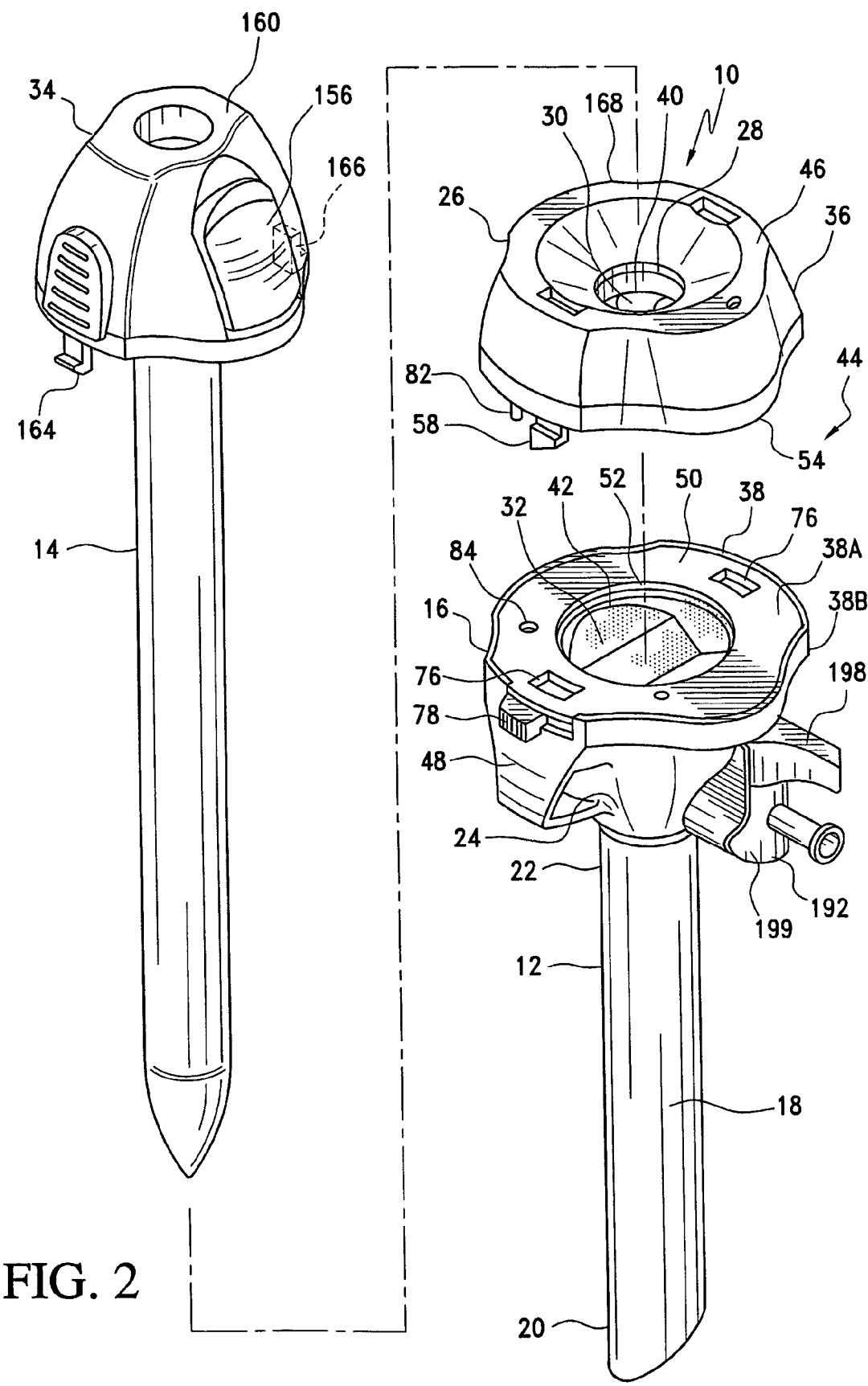
FIG. 2 is an exploded view of the trocar assembly shown in FIG. 1.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

A protector for a trocar seal assembly in accordance with the present invention is disclosed. The protector provides for improved resistance to tearing by protecting the seal from direct contact with obturators and tools as they pass through the trocar cannula. As those skilled in the art will certainly appreciate, the present protector may be adapted for use with a variety of trocar assemblies without departing from the spirit of the present invention.

Referring to FIGS. 1 to 5, the trocar assembly 10 generally includes a trocar cannula 12, a trocar obturator 14, and a trocar housing (or handle) 16. The trocar cannula 12 defines an interior lumen 18 having an open distal end portion 20 and an open proximal end portion 22. The proximal end portion 22 extends into and is mounted in the distal end portion 24 of trocar housing 16. The trocar housing 16 has an open proximal end portion 26 that defines an opening 28. The opening 28 is provided with a proximal seal assembly 30 constructed in accordance with the present invention and described in detail hereinbelow. The opening 28 is further provided with a duckbill seal assembly 32 positioned beneath the proximal seal assembly 28. While the present seal assembly is disclosed as a proximal seal assembly forming part of a dual sealing system, the present seal assembly may be utilized in a single seal system without departing from the spirit of the present invention.

In general, the trocar sleeve 44 is composed of a trocar cannula 12 and a trocar housing 16. The trocar housing 16 includes a first housing member 36 and a second housing member 38. The second housing member 38 is ultimately composed of a second housing member cover 38a and a second housing member base 38b. Although, the housing 16 is disclosed as two components it is contemplated that a single component could be used without departing from the spirit of the present invention. The two component housing shown, aids in removal of specimens.

The trocar obturator 14 is slidable in and removable from within the trocar cannula 12 and is inserted into the trocar housing 16 and the trocar cannula 12 through the proximal seal assembly 30, the duckbill seal assembly 32 and the opening 28 of the trocar housing 16. An obturator handle 34 is provided at the proximal end of the trocar obturator 14 and a point or blade (not shown) is formed at the distal end thereof. As is well known in the art, the proximal seal assembly 30 cooperates with the exterior of the instruments (for example, trocar obturators and other tools adapted for use in conjunction with trocar based procedures) extending through the trocar sleeve 44 to sealingly engage the exterior surface thereof and thereby preclude the passage of fluids through the trocar housing 16.

Rotational Latching System

With regard to the trocar housing 16 and with reference to FIGS. 1 to 5, the trocar housing 16 is constructed of a first housing member 36 and a second housing member 38 which are selectively coupled for reasons that will be discussed below in greater detail. The first and second housing members 36, 38 include aligned apertures 40, 42 shaped and dimensioned for the receipt of instruments that are selectively passed through the trocar housing 16.

As those skilled in the art will certainly appreciate, it is important that the first and second housing members 36, 38 remain securely attached during the insertion of the trocar sleeve 44 into the abdominal wall, as well as during the normal course of a procedure. However, it is also desirable to remove the first housing member 36 during the removal of a specimen, for example, from the abdominal cavity. The removal of the first housing member 36 allows the specimen to pass through only the duckbill seal assembly 32, instead of passing through both the duckbill seal assembly 32 and the proximal seal assembly 30. This provides for easier specimen removal and less trauma to the specimen during the removal process.

The first housing member 36 supports the proximal sealing assembly 30 and sits atop the second housing member 38 in which the duckbill seal assembly 32 is mounted. The first housing member 36 includes an aperture 40 extending therethrough. The proximal seal assembly 30 is positioned within the aperture 40 of the first housing member 36.

As to the second housing member 38, the second housing member 38 includes an aperture 42 extending therethrough. The duckbill seal assembly 32 is positioned within the aperture 42 of the second housing member 38 adjacent the top surface 50 of the second housing member 38. In fact, and for reasons which will be discussed below in greater detail, the peripheral rim 52 of the duckbill seal assembly 32 is positioned directly adjacent the top surface 50 of the second housing member 38 for engagement with the lower surface 54 of the first housing member 36.

Connection of the first housing member 36 to the second housing member 38 is facilitated by a rotary latch mechanism 56. In particular, the first housing member 36 includes first and second downwardly extending arms 58. Each of the downwardly extending arms 58 includes a downwardly facing camming surface 60 and an outwardly facing latching surface 62.

The second housing member 38 similarly includes a latching ring 64 with first and second latch members 66 for respectively engaging the respective latching surfaces 62 of the first and second downwardly extending arms 58 of the first housing member 36. The latching ring 64 is axially aligned with the central axis of the trocar sleeve 44 and lies in an annular groove 68 around the perimeter of the duckbill seal assembly 32. Although the latching ring 64 in accordance with a preferred embodiment rotates about a central axis of the trocar housing 16, the latching ring 64 may rotate about other axes without departing from the spirit of the present invention. The latching ring 64 is capable of rotating about the central axis of the trocar sleeve 44, but is attached to the trocar housing 16 by a spring 70. The spring 70 holds the latching ring 64 in a locked position with a small amount of preloaded bias. However, the spring 70 allows rotation of the latching ring 64 during the attachment of the first housing member 36. The first and second latch members 66 respectively include upwardly facing camming surfaces 72 that interface with downwardly facing camming surfaces 60 of the first and second downwardly extending arms 58 of the first housing member 36.

The first and second latch members 66 each include an upwardly facing camming surface 72 shaped and dimensioned to respectively engage the camming surfaces 60 of the downwardly extending arms 58. Similarly, the first and second latch members 66 include inwardly facing latching surfaces 74 shaped and dimensioned for engaging the outwardly facing latching surfaces 62 of the first and second downwardly extending arms 58.

In practice, latching of the first and second housing members 36, 38 is achieved by passing the first and second downwardly extending arms 58 through holes 76 formed in the top surface 50 of the second housing member 38. As the first and second downwardly extending arms 58 extend through the respective holes 76 adjacent the first and second latch members 66 of the latching ring 64, the camming surfaces 60 of the respective first and second downwardly extending arms 58 engage the camming surfaces 72 of the first and second latch members 66. The engagement causes the latch ring 64 to rotate in a manner permitting the first and second downwardly extending arms 58 to extend past the first and second latch members 66. This rotation is against the bias provided by the spring 70.

Once the first and second downwardly extending arms 58 move past the first and second latch members 66, the spring 70 biasing the latching ring 64 causes the latching ring 64 to return to its original position and the outwardly facing latching surfaces 62 of the first housing member 36 engage the inwardly facing latching surfaces 74 of the second housing member 38 to securely couple the first housing member 36 to the second housing member 38. The first and second housing members 36, 38 are selectively disengaged through the actuation of a lever 78 attached to the latching ring 64. Rotation of the lever 78 causes the latching ring 64 to rotate, moving the first and second latching members 66 out of engagement with the downwardly extending arms 58.

The top surface 50 of the second housing member 38 includes holes 76 allowing the downwardly extending arms 58 of the first housing member 36 to pass through with only a small amount of clearance. This limited clearance allows for very little movement of the downwardly extending arms 58 either in the plane of the holes 76 or in bending. Therefore, when the first housing member 36 is latched to the second housing member 38, the only means of forceful disassembly of the first and second housing members 36, 38 is by shearing the first and second downwardly extending arms 58 themselves or by pure tension on the legs themselves. The first and second arms 58 cannot bend out of the way or slip due to the size of the holes 76. This creates a very secure attachment. The trocar housing 16 is disassembled by pushing the lever 78 in a horizontal rotation, causing rotation of the latching ring 64 about the central axis of the trocar sleeve 44 in a manner overcoming the spring force. The lever 78 is accessible to the surgeon through a slot in the side of the trocar housing 16. When the lever 78 is pressed, the first and second latching members 66 of the latching ring 64 rotate past the first and second downwardly extending arms 58, and the first housing member 36 is released from the second housing member 38.

The first housing member 36 is attached to the second housing member 38 by a rotary latch mechanism 56 and a seal between the first and second housing members 36, 38 is required to maintain insufflation. This seal is accomplished by using a downwardly extending flange 80 on the lower surface 54 of the first housing member 36 to compress a portion of the duckbill seal assembly 32 adjacent the top surface 50 of the second housing member 38. The flange 80 and the duckbill seal assembly 32 include opposed angled surfaces. This provides an angular interface between the flange 80 on the first housing member 36 and the duckbill seal assembly 32 interface of the second housing member 38. This provides easier attachment of the first housing member 36 and permits vertical travel beyond the distance required to seal with no effect on the duckbill seal assembly's performance capabilities. In fact, this over travel is required to provide functional reliability in the rotary latch mechanism.

The downwardly extending flange 80 of the first housing member 36 includes an angular interface that exerts a radial force component on the duckbill seal assembly 32. The angular interface also creates a vertical force component that translates into assembly force. The radial force dilates the interfacing feature, that is, the peripheral rim 52 of the duckbill seal assembly 32. Since the vertical force is only a portion of the total normal force, the assembly force is reduced as a function of the angle of the interface.

In addition to the radial and vertical forces, the seal between the first and second housing members 36, 38 generates a camming action due to the interaction between the downwardly extending flange 80 and the peripheral rim 52 of the duckbill seal assembly 32. The radial movement of the peripheral rim 52 of the duckbill seal assembly 32 allows a small amount of over travel for the flange 80 with no negative impact to the duckbill seal assembly's ability to seal as intended for normal operation.

In addition to providing for over travel, the compression of the peripheral rim 52 of the duckbill seal assembly 32 stores energy assisting in the disengagement of the first housing member 36 from the second housing member 38. The stored energy causes the first housing member 36 to readily move from the second housing member 38 upon actuation of the lever 78.

More particularly, coupling of the first and second housing members 36, 38 is enhanced by the provision of a downwardly extending flange 80 along the lower surface 54 of the first housing member 36 that is shaped and dimensioned for engaging the peripheral rim 52 of the duckbill seal assembly 32. With this in mind, the downwardly extending flange 80 is provided with an inwardly facing taper and the peripheral rim 52 is provided with an outwardly facing taper. The inwardly and outwardly facing tapers interact to permit play between the first and second housing members 36, 38 in a manner facilitating secure attachment. By providing opposed tapered surfaces, and in particular by providing an inwardly tapered surface on the peripheral rim 52 with a slight amount of give under pressure, the dimensional tolerances necessary for ensuring coupling of the latch mechanisms are enhanced.

Proper alignment between the first and second housing members 36, 38 is achieved by the provision of an alignment pin 82 extending downwardly from the lower surface 54 of the first housing member 36 and a mating hole 84 shaped and dimensioned for receiving the alignment pin 82 formed along the top surface 50 of the second housing member 38. The provision of the alignment pin 82 and the mating hole 84 ensures that the first and second housing members 36, 38 may only be assembled in the desired configuration. Optionally, a second pin may be provided to prevent the opposite latch from engaging. This is an integral part of the design as it is intended for safety. The trocar obturator 14 can only be attached to the first housing member 36 in one configuration and the first housing member 36 can only be attached to the second housing member 38 in one configuration.

As discussed above, the rotary latch mechanism 56 utilized in connecting the first housing member 36 to the second housing member 38 offers a wide variety of advantages. In particular, the rotary latch design allows the first housing member 36 to be rigidly attached to the second housing member 38 with no chance of the latches "slipping off", while allowing very easy detachment of the first housing member 36. In fact, the holes 76 through which the first and second downwardly extending arms 58 of the first housing member 36 pass through disallows any chance of the arms 58 bending out of the way. In addition, since the force vector of the latch return spring 70 is perpendicular to any disengaging force exerted during use, the force required to attach the first housing member 36 can be addressed independently of any specified disengaging force. This is contrary to typical latch designs where the arms of the latches are elastically bent to attach and detach the outer seal housing. In these types of designs the force of assembly and the force of disassembly are directly linked to one another via the bending characteristics of the latching arms. Finally, the latch mechanism is easily manipulated with one hand.

With regard to the angular contact between the downwardly extending flange 80 of the first housing member 36 and the peripheral rim 52 of the duckbill seal assembly 32, this provides for reduced assembly force required in attaching the first housing member 36 to the second housing member 38. One may compress the first housing member 36 a greater distance than with a flat seal and still get the same force of assembly. This allows tolerances of design parts to be greater for given compression distance requirements. In addition, the raised nature of the peripheral rim 52 on the duckbill seal assembly 32 allows for radial deflection as well, thereby, additionally reducing assembly forces.

Reinforced Seal Assembly

Referring to FIGS. 6 to 10, the proximal seal assembly 30 is disclosed. The seal assembly generally includes a cap 86, a crown 88, bellows 90 used for radial seal movement, a female retaining ring 92, a protector 94, a plurality of reinforced seal segments 96 making up a seal body 98, a male retaining ring 100 and a bottom body 102. The reinforced seal segments 96 are positioned as described below in greater detail and mounted between the retaining rings 92, 100 for creating a seal assembly 30 in accordance with the present invention.

More particularly, and with reference to FIGS. 7 to 10, a reinforced seal segment 96 is shown. As is described in greater detail below, the proximal seal assembly 30 employs a plurality of reinforced seal segments 96 in creating a complete seal body 98. Each of the reinforced seal segments 96 is in the form of a partial cone, in particular, a cone extending about approximately 225 degrees. While the partial cone shape in accordance with a preferred embodiment of the present invention employs partial cones extending about approximately 225 degrees, partial cones of other shapes may be employed without departing from the sprit of the present invention. Although cone shaped seal segments are disclosed in accordance with a preferred embodiment, flat seal segments could be employed without departing from the spirit of the present invention.

Each reinforced seal segment 96 is preferably manufactured from an elastomer of a cross linked polymer, such as, but not restricted to, polyisoprene or silicone. However, those skilled in the art will appreciate that other materials may be employed without departing from the spirit of the present invention.

In practice, a series of reinforced seal segments 96 are utilized in the creation of a seal body 98 through which an instrument may be inserted. In accordance with a preferred embodiment of the present invention, four reinforced seal segments 96 are aligned and successively shifted 90 degrees relative to each other. The seal segments 96 are arranged in a "woven" manner. That is, each seal segment 96 includes a first side 104 and second side 106, and the first side 104 of each seal segment 96 is placed atop the second side 106 of the adjacent seal segment 96 to create a "woven" assembly of seal segments 96.

The reinforced seal segments 96 are then bound together along their peripheral edges 108 to the male and female retaining rings 94, 100 to create a complete seal body 98. As a result of the partial cone shape of the reinforced seal segments 96 and the relative rotation thereof, the bound seal segments 96 create a seal body 98 wherein the individual seal segments 96 are pushed outwardly upon the insertion of an instrument to create an opening for the passage of instruments and resilient move inwardly to close the opening upon the removal of instruments. The typical deformation of the reinforced seal segment 96 is shown with reference to FIG. 3. The deformation is shown with the insertion of an instrument therethrough.

As mentioned above, each of the reinforced seal segments 96 is generally in the form of a cone with a portion of the cone cut away. The reinforced seal segment 96 includes a peripheral edge 108 secured to a central seal member 110. The peripheral edge 108 is substantially flat, lying in the same plane, while the central seal member 110 is formed in the shape of a section of a cone.

The central seal member 110 is enhanced through the inclusion of a reinforcement pad 112 at a central position on the reinforced seal segment 96. That is, the reinforcement pad 112 is positioned between the peripheral edge and the free edge of the central seal member 110. More particularly, the reinforcement pad 112 is positioned at the tip of the cone defined by the central seal member 110 with edges of the reinforcement pad 112 being aligned with the free edge of the central seal member 110 at the tip of the cone.

The reinforcement pad 112 is integrally formed with the remainder of the central seal member 110, but has a thickness that is approximately 2.5 times that of the nominal thickness of the central seal member 110. In particular, the reinforcement pad 112 of the central seal member 110 is formed with a thickness of approximately 0.017 inches, while the remainder of the central seal member 110 is formed with a thickness of approximately 0.007 inches. While thicknesses are disclosed above in accordance with a preferred embodiment of the present invention, different thickness may be employed without departing from the spirit of the present invention. The transition between the reinforcement pad 112 and the remainder of the central seal member 110 is achieved by tapering the central seal member 110 between the thickness of the reinforcement pad 112 and the remainder of the central seal member 110. It is further contemplated, that the transition could be done without transition regions; that is with a sharp transition. However, the preferred embodiment has no stress risers and allows the seal to seal better. It is also contemplated that the seal segments could have been made with the pad flat with no transition.

Figure 7:
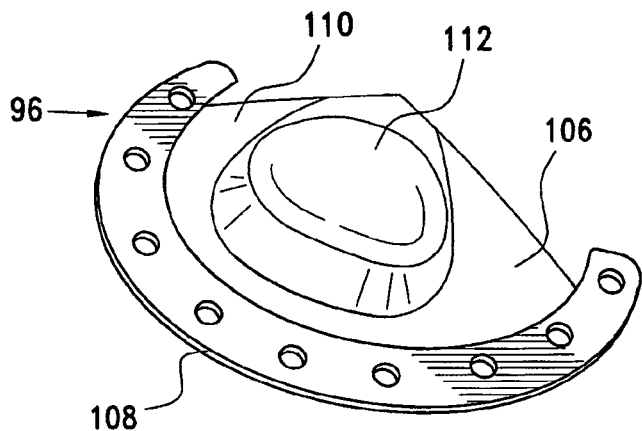
FIG. 7 is a bottom perspective view of a seal segment.
Figure 8:
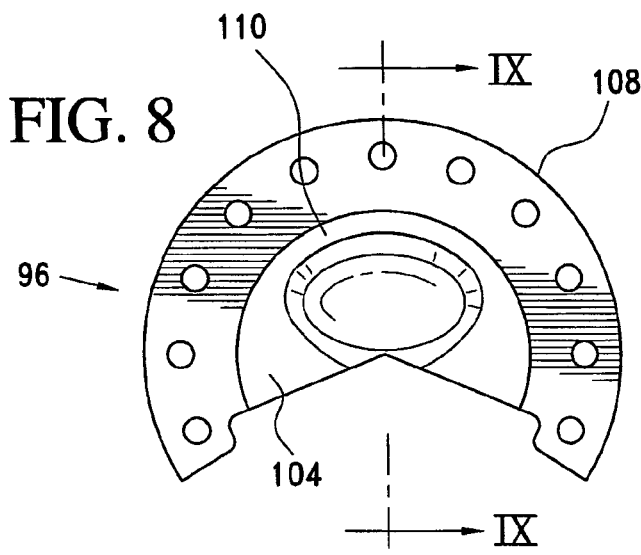
FIG. 8 is a top view of a seal segment.
Figure 9:
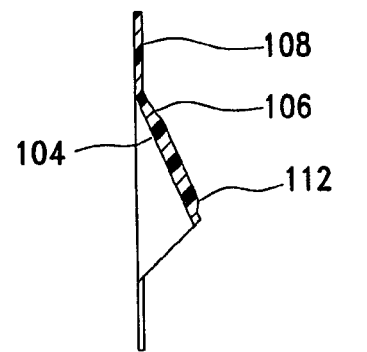
FIG. 9 is a cross sectional view along the line IX-IX in FIG. 8.
Figure 10:
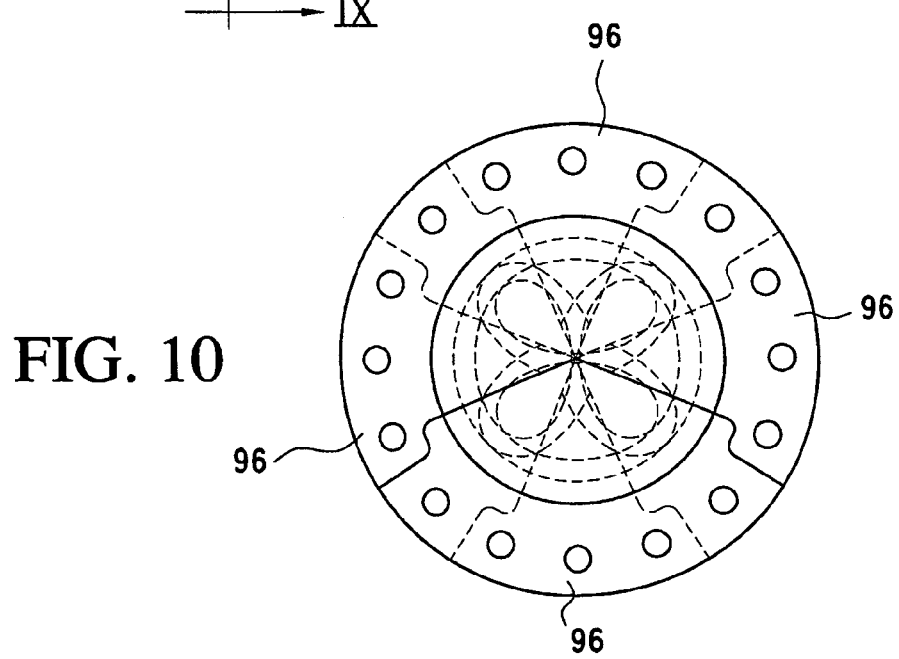
FIG. 10 is a seal body composed of four seal segments as shown in FIGS. 7, 8 and 9.
Figure 11:
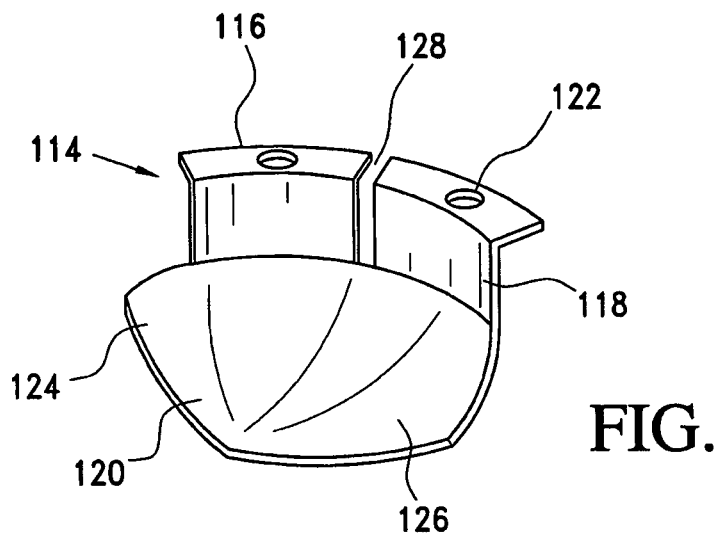
FIG. 11 is a top perspective view of a protector segment.
Figure 12:
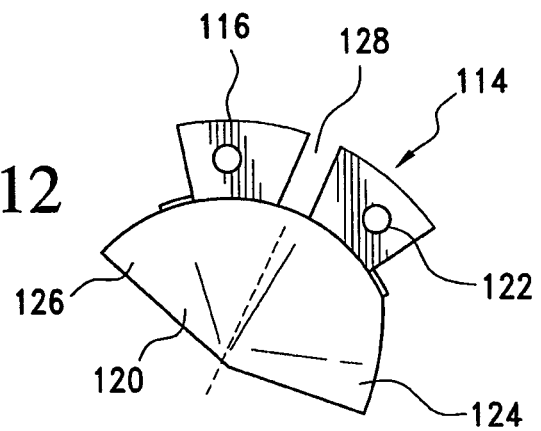
FIG. 12 is a bottom view of a protector segment.

As shown in FIG. 7, and in accordance with a preferred embodiment of the present invention, the reinforcement pad 112 is general formed in a triangular configuration along the center of the arc defined by the reinforced seal segment 96. In particular, the reinforcement pad 112 occupies an arc of approximately 90 degrees along the central seal member 110. As those skilled in the art will certainly appreciate, the shape and size of the reinforcement pad 112 may be varied to suit specific needs without departing from the spirit of the present invention. However, the reinforcement pad 112 should be shaped and dimensioned to cover an area that is intended for contact with instruments being passed through the trocar assembly 10.

The reinforcement pad 112 is located on a portion of the central seal member 110 that is most likely to have direct contact with surgical instruments as they are inserted within the trocar cannula 12. In accordance with a preferred embodiment of the present invention, the reinforcement pad 112 is centrally located, as most surgical instruments will be inserted through the center of the trocar housing 16 and the trocar cannula 12.

It should be noted that in other embodiments the angled surface that slopes from the reinforcement pad 112 to the nominal thickness of the central seal member 110 could be omitted and the reinforcement pad 112 could be smoothly blended into the nominal thickness of the central seal member 110 via continuous curvature.

Low drag forces between the proximal seal assembly 30 and an insertion instrument are desirable. The present proximal seal assembly 30 permits the production of low drag forces without reducing seal durability. This is accomplished by reducing the seal thickness in conjunction with application of a reinforcement pad 112 as described above. As such, the reduction in thickness (in the area that is not contacting the instrument) is not accompanied with a reduction in seal durability as is common with prior art seal assemblies.

Seal assemblies incorporating reinforcement pads 112 in accordance with the present invention greatly reduce snagging and tearing the seal through either the insertion or withdrawal of an instrument without requiring additional thickness throughout the seal segments 96. The greater thickness in the region of the reinforcement pad 112 resists tenting at the reinforcement pad 112 where the instrument is contacting the seal assembly 98. However, the thin sections of the central seal member 110 surrounding the central reinforcement pad 112 allow for easy stretching of the remainder of the central seal member 110, thereby keeping drag forces on moving instruments to a minimum. Since the greatest strain occurs along the opening of the central seal member 110 when an instrument is present, and in accordance with a preferred embodiment, the reinforced seal segments 96 should be kept thin in any areas not contacting an instrument. This minimizes drag forces.

The effective protection imparted by the present reinforcement pad 112 manifests itself in the proximal seal assembly 30 as follows. For a given deflection of the proximal seal assembly 30 due to initial contact with the tip of an instrument, the region defined by the reinforcement pad 112 of the proximal seal assembly 30 will have a relatively low strain when compared to the thinner portion of the central seal member 110 surrounding the reinforcement pad 112 due to the difference in thicknesses between the reinforcement pad 112 and the central seal member 110. This differential in strain is largest at the opening of the proximal seal assembly 30, where overall strains are highest. When force is applied to the reinforcement pad 112 due to contact with an instrument, the increased thickness of the reinforcement pad 112 will resist tenting, while the thin cross section of the remainder of the central seal member 110 not covered by the reinforcement pad 112 will allow the reinforcement pad 112 to easily deflect distally permitting the tip of the instrument to roll into the center of the proximal seal assembly 30. Resistance to tearing for the reinforced seal segment 96 is greatly increased as compared to prior art seal segments.

The reinforcement pads 112 allow the reinforced seal segments 96 to protect themselves against sharp instruments independently of other peripheral protection devices. This protection is integral to the reinforced seal segments 96 themselves. Also the addition of reinforcement pads 112 at strategic locations (away from areas of high strain directly located at the point of likely sharp instrument contact) allows the reinforcement pads 112 to protect against puncture with little or no impact to seal performance. It does not increase peak instrument insertion forces or instrument drag forces. It is contemplated that the use of reinforcement pads 112 might be expanded beyond positioning at a central location, thereby offering some impact to peak instrument insertion forces and instrument drag forces. However, due to the nature of the seal segments 96 and their greatly reduced strain relative to standard lip seals, this impact would likely yield a design that would easily outperform standard seal assemblies.

Woven Seal Protector

Figure 13:
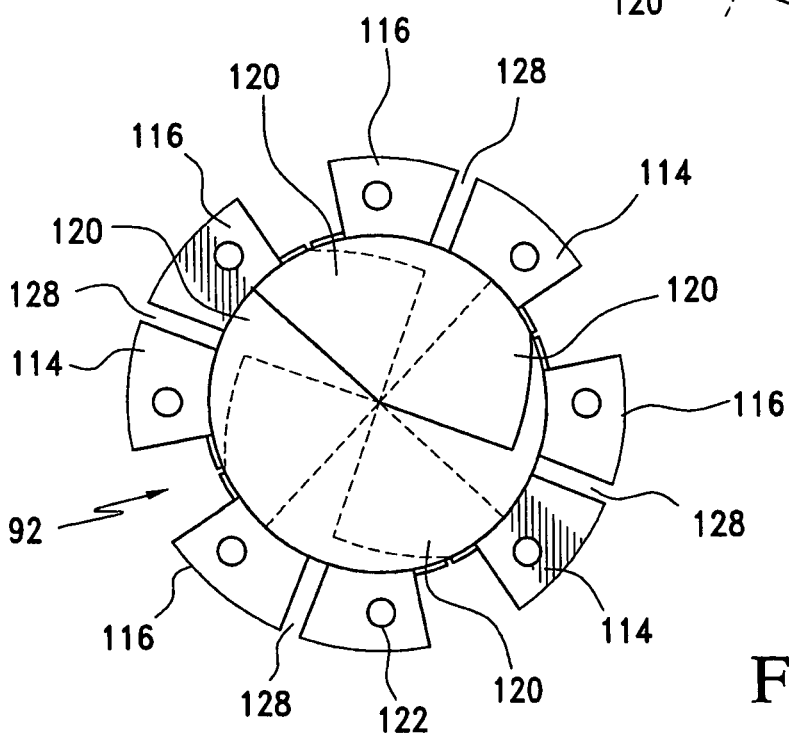
FIG. 13 is protector composed of four protector segments as shown in FIGS. 11 and 12.

Although the seal body 98 is formed with reinforcement pads 112 as described above it is still desirable to provide the proximal seal assembly 30 with a protector 92, as best shown in FIG. 13. The protector 92 in accordance with a preferred embodiment of the present invention is positioned directly above the seal body 98. With reference to FIGS. 6 and 11-13, the protector 92 is composed of multiple overlapping protector segments 114 assembled in a woven arrangement to provide a complete protector 92. By forming the protector 92 in a woven arrangement, additional protector material is added (as a result of the overlapping arrangement) such that additional surface area of the seal body 98 may be protected as the protector segments 114 separate as an instrument is inserted into the seal.

As the present proximal seal assembly 30 has a small central opening which expands in a reliable and convenient manner, the protector 92 must be formulated to close gaps between protector segments 114 as an instrument is passed through the protector 92 and the seal body 98. This requires the addition of material along the opening of the protector 92.

In accordance with the present invention, additional material is added to the protector 92 by weaving a plurality of protector segments 114. By weaving the protector segments 114, extra material is added to the protector 92 so as to widen each protector component while still allowing the protectors to fit within the coned seal profile. The extra material is wrapped behind the protector segment 114 to one side of each protector segment 114. This extra material is not visible when the protector segments 114 are viewed from above without an instrument inserted.

The protector segments 114 in accordance with a preferred embodiment of the present invention are manufactured from molded elastomer, for example, pellethane. However, it is not intended that the protector segments 114 be limited to merely elastomers, but the protector segments 114 may be made from any type of material that contains the required properties and characteristics for the function described herein.

In particular, four protector segments 114 are arranged to create the protector 92. While four protector segments 114 are utilized in accordance with a preferred embodiment of the present invention, the protector 92 may ultimately be formed with different numbers of protector segments 114 without departing from the spirit of the present invention.

Each protector segment 114 is semicircular when viewed from above and is generally in the form of a partial cone. Each of these protector segments 114 include a substantially round peripheral edge 116, a support wall 118 extending from the peripheral edge 116 and a cone shaped protector member 120. The cone shaped protector member 120 opposite the support wall 118 and the peripheral edge 116 defines straight shaped edge 121.

In accordance with a preferred embodiment of the present invention, the cone shaped protector member 120 spans an arc of approximately 180 degrees, while the support wall 118 and the peripheral edge 116 span an arc of approximately 120 degrees along the center of the cone shaped protector member 120. As will be discussed below in greater detail, the limited arc spanned by the peripheral edge 116 and the support wall 118 reduces undesirable forces as instruments are moved past the proximal seal assembly 30.

The outer peripheral edge 116 is adapted for positioning within the first housing member 36. The outer peripheral edge 116 further includes a series of apertures 122 that function as a means of attachment for the protector segments 114. As will be apparent based upon the following disclosure, the use of multiple protector segments 114 defining an arc of approximately 180 degrees results in a reduction in hoop stresses by providing a protector 92 composed of a series of protector segments 114 which readily bend in and out radially as instruments are inserted therethrough.

Each protector segment 114 includes a first section 124 and a second section 126 defining opposite sides of the protector segment 114. The four individual protector segments 114 are combined in a woven arrangement to create a complete protector 92 that fully protects the underlying seal body 98. That is, the protector 92 is assembled by placing the first section 124 of a first protector segment 114 upon the second section 126 of a second protector segment 114. The first section 124 of the second protector segment 114 is subsequently placed upon the second section 126 of a third protector segment 114, the first section 124 of the third protector segment 114 is placed upon the second section 126 of a fourth protector segment 114 and the first section 124 of the fourth protector segment 114 is placed upon the second section 126 of the first protector segment 114 like one folds the final flap of a box lid.

The protector segments 114 are ultimately held together through the application of the crown 88 and female retaining ring 94. Retaining members are well known to those skilled in the art and a variety of retaining members may be employed within the spirit of the present invention.

As those skilled in the art will readily appreciate, movement of the cone shaped protector members 120 relative to the peripheral edge 116 and the support wall 118 is subject to resistance based upon the various orientations of the connected components. As such, the cone shaped protector members 120 might be susceptible to buckling as instruments are moved through the proximal seal assembly 30.

This resistance to movement is minimized due to the limited arc of the peripheral edge 116 and the support wall 118 as discussed above. In addition, the resistance is further minimized by forming a central slot 128 with the peripheral edge 116 and/or the support wall 118. This slot 128 functions to reduce buckling as the protector members 120 may move the same distance with less resistance.

By weaving the protector 92 additional material may be added to each protector segment 114 while still allowing the distal end of the protector 92 to fit into the apex of the cone shaped seal body 98. This is accomplished by having the extra material added to the protector segments 114 wrap behind the protector segment 114 adjacent thereto. This extra material allows for improved coverage of the seal body 98, especially when instruments are inserted at an angle relative to the proximal seal assembly 30. Finally, weaving of the protector 92 has minimal, if any effects on the instrument drag force as it is moved in and out of the proximal seal assembly 30. This is a result of the fact that the protector segments 114 move easily relative to each other.

In practice, and due to the extra material added to each protector segment 114, as an instrument is inserted into the protector 92, the protector segments 114 spread, exposing the additional protector material positioned behind adjacent protector segments 114. This additional material continues to cover the seal body 98 as the protector segments 114 bend relative to one another. The less seal body 98 material exposed to the inserted instrument, the better the protection offered by the present protector 92. While the present protector 92 offers good seal protection, additional protector segments 114 can be added although they might cause an increase in the instrument drag forces. This may be balanced, however, by thinning the protector segments 114 to make them more flexible or by adding lubricant to the protector segments 114 and/or the seal body 98.

Duckbill Seal Assembly

Figure 14:
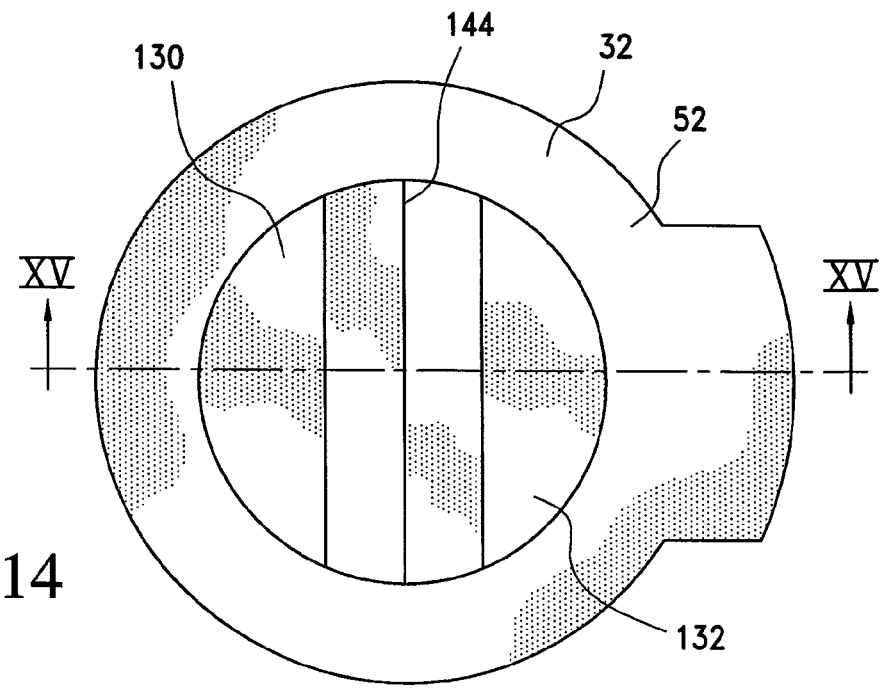
FIG. 14 is a top perspective view of a duckbill seal assembly in accordance with the present invention.
Figure 15:
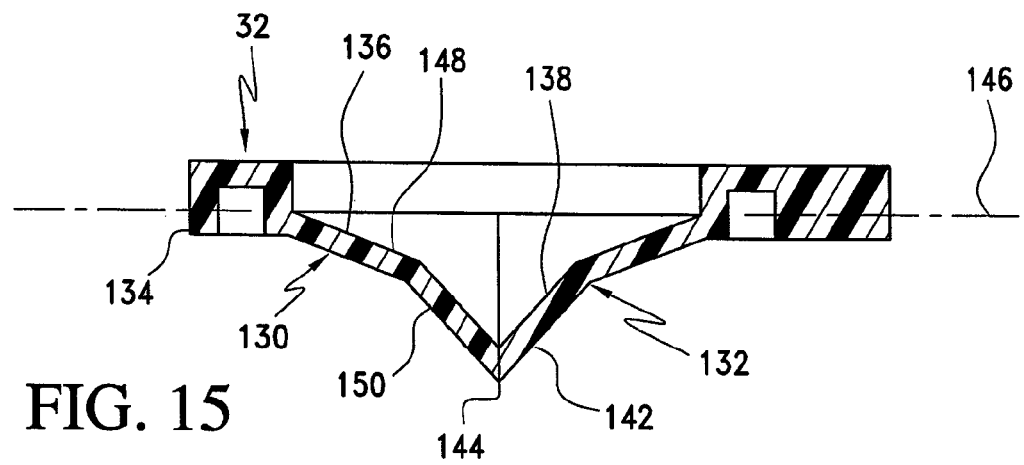
FIG. 15 is a cross sectional view along the line XV-XV of FIG. 14.
Figure 16:
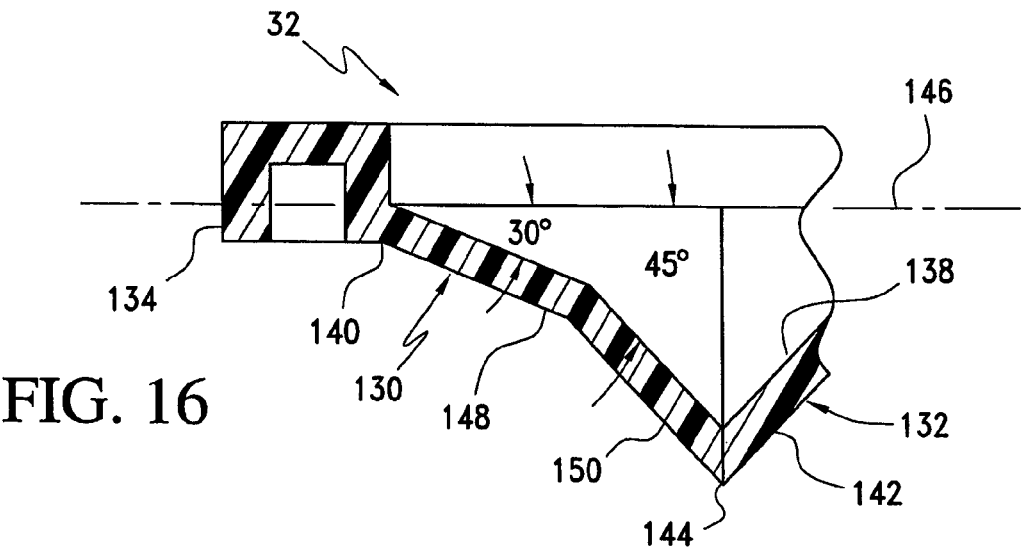
FIG. 16 is a partial cross sectional view along the line XV-XV of FIG. 14.
Figure 17:
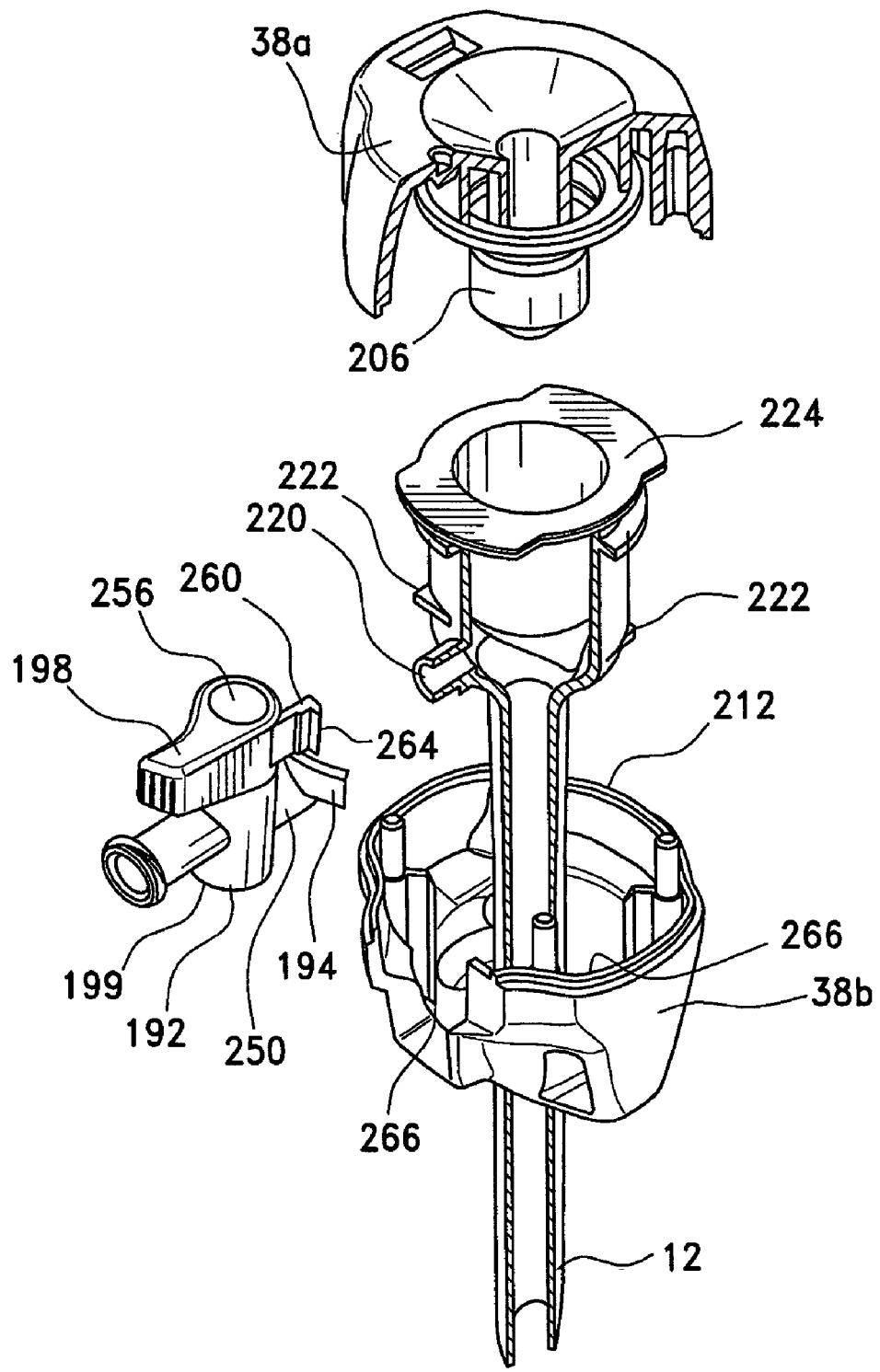
FIG. 17 is an exploded view of the trocar sleeve in accordance with the present invention.
Figure 18:
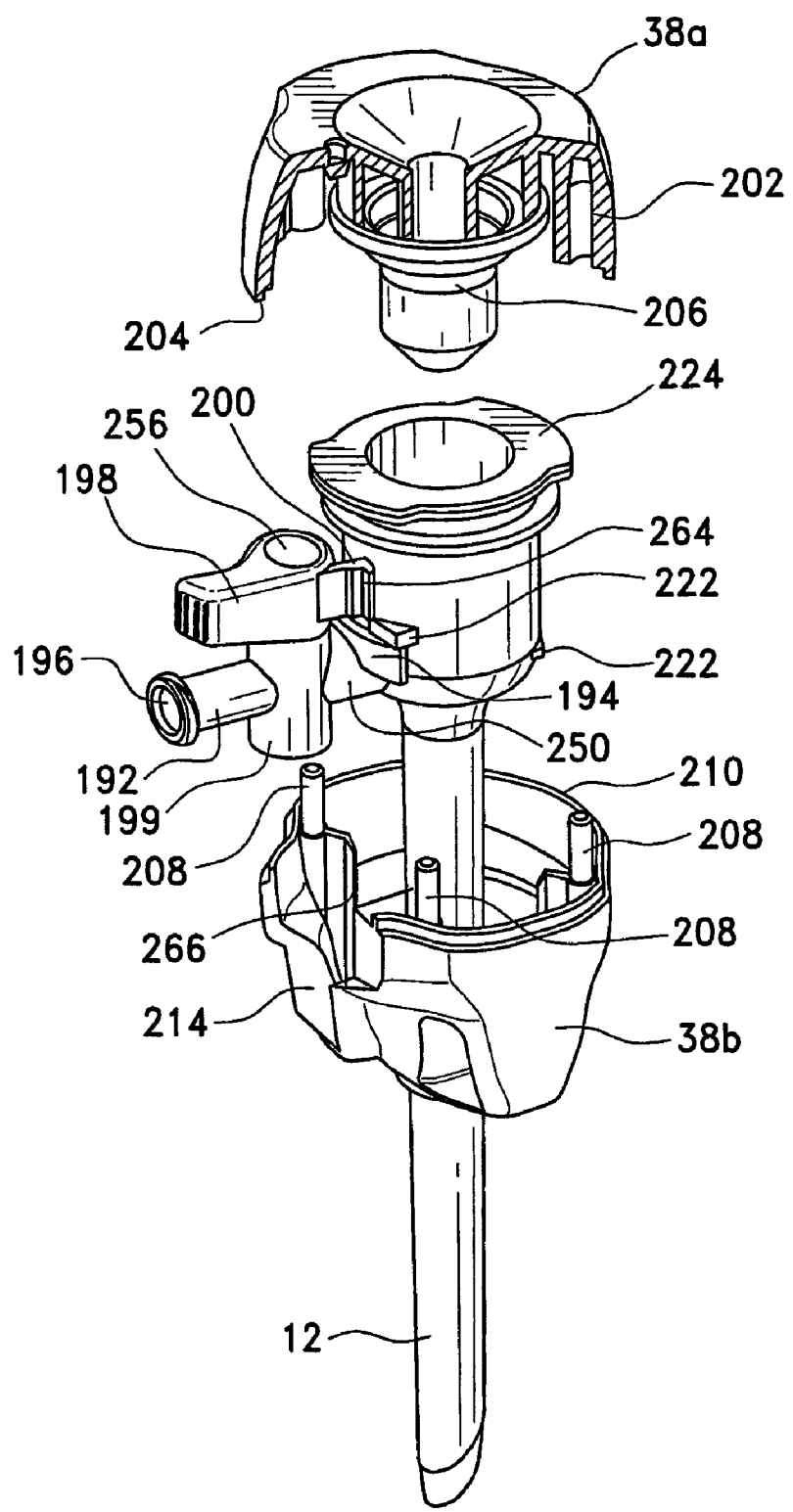
FIG. 18 is a further exploded view of the trocar sleeve in accordance with the present invention.
Figure 19:
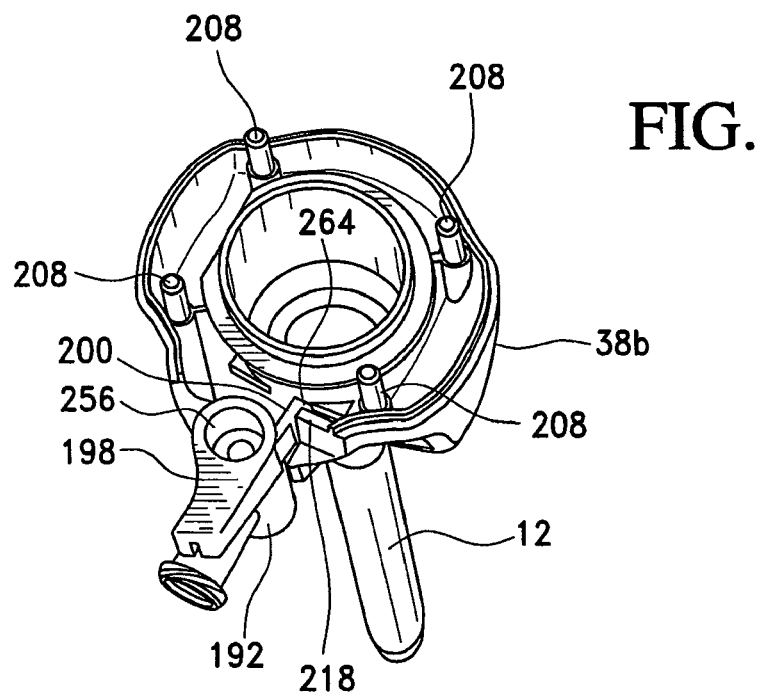
FIG. 19 is an assembled perspective view of the trocar sleeve shown in FIGS. 17 and 18.
Figure 20:
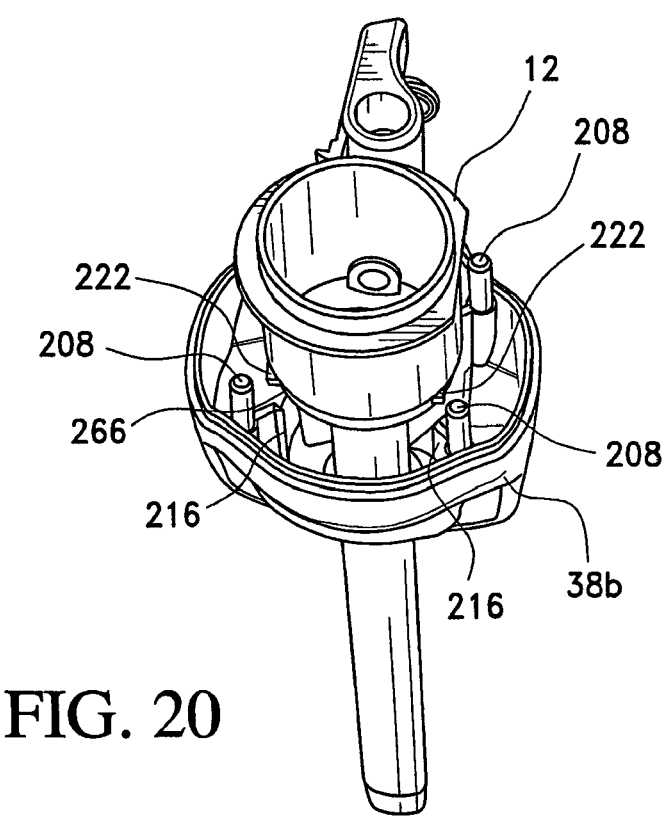
FIG. 20 is a rear perspective view of the trocar sleeve shown in FIGS. 17 and 18.

As mentioned above, a duckbill seal assembly 32 is housed within the second housing member 38. With reference to FIGS. 14 to 16, the duckbill seal assembly 32 in accordance with a preferred embodiment of the present invention is disclosed. The duckbill seal assembly 32 includes first and second seal bodies 130, 132 extending from a circumferential flange member 134 shaped and dimensioned for mounting within the second housing member 38.

Each of the first and second seal bodies 130, 132 includes an upper surface 136, 138 and a lower surface 140, 142. The upper surface 136, 138 and the lower surface 140, 142 are generally mirror images as the first and second seal bodies 130, 132 maintain a substantially consistent thickness along its entire length with the exception of the reinforcing rib along the upper surface 136, 138.

The first and second seal bodies 130, 132 are mounted within the trocar housing 16 for movement as an instrument is passed therethrough. With this in mind, the proximal end of each of the first and second seal bodies 130, 132 is coupled to the trocar housing 16 via the circumferential flange 134, while the distal ends of the first and second seal bodies 130, 132 intersect to define an abutment face 144. The abutment face 144 is generally positioned within the center of the trocar housing 16 to permit the passage of an instrument therethrough, while in the absence of such an instrument the abutment face 144 is closed via the resilience of the first and second bodies 130, 132 as they are biased under the pressure generated from the body cavity in which the trocar assembly 10 is positioned. For example, biased under the pressure from the abdominal insufflation gas pressure. This pressure causes the duckbill seal assembly 32 to move to a closed position with the distal ends of the first and second seal bodies 130, 132 in contact.

As those skilled in the art will certainly appreciate, the seal bodies 130, 132 may be formed with ribs (not shown) on the upper surface 136, 138 so as to enhance the stability of the seal bodies 130, 132 when contacted with an instrument. The ribs also provide a path for instruments to ride upon as they pass through the duckbill seal assembly 32. The ribs also lower friction as the instruments pass through the duckbill seal assembly 32 because it provides less surface area on which an instrument may ride, and thus greater contact pressure between the seal and the instrument may be applied.

The first and second seal bodies 130, 132 will now be described with reference to the first seal body 130. Those skilled in the art will appreciate that the first and second seal bodies 130, 132 are identical and the following descriptions equally relates to the second seal body 132. The seal body 130 is formed with a first section 148 and a second section 150 angularly oriented relative to each other and a transverse plane 146 extending through the circumferential flange 134.

In particular, the transverse plane 146 is substantially perpendicular to the longitudinal axis extending through the duckbill seal assembly 32. The first and second sections 148, 150 extend from a proximal end of the seal body 130 respectively toward a distal end of the seal body 130. As such, the first section 148 is positioned adjacent the proximal end of the seal body 130 adjacent the wall of the circumferential flange 134 and the trocar housing 16. The first section 148 moves only slightly as an instrument is inserted therethrough. The second section 150 is positioned adjacent the distal end of the seal body 130 and adjacent the abutment face 144. The second section 150 freely moves as an instrument is inserted therethrough.

In general, the first and second sections lie at angles between 0 degrees and 90 degrees relative to the transverse plane. Assuming the transverse plane 146 lies in a horizontal plane, and in accordance with a preferred embodiment of the present invention, the first section 148, which begins at the proximal end of the seal body 130, is oriented at approximately a 30 degree angle relative to the horizontal plane in which the transverse plane 146 lies. The second section 150, which extends to the distal end of the seal body 130, is thereafter oriented at a 45 degree angle relative to the horizontal plane. Those skilled in the art will appreciate that the angles disclosed above in accordance with a preferred embodiment of the present invention may be varied without departing from the spirit of the present invention. The chosen angles are based upon the trade off between the durability of the seal bodies (improves at greater angles as likelihood of an instrument pointedly engaging the seal, i.e. tenting is less likely at greater angles) and the height of the seal (greater angles dictate greater height). For example, it is contemplate the second section 150 may be formed at an angle of approximately 40 degrees to approximately 50 degrees while providing for the many advantages contemplated in accordance with the present duckbill seal assembly 32. The height or profile of the duckbill seal assembly 32 is important as reductions in size allow for improved instrument access because the length of the trocar housing 16 may be consequently made smaller. Smaller housings provide surgeons with greater access within the body cavity and thus are very desirable.

While a preferred embodiment as described above employs first and second sections 148, 150 in implementing the present invention, additional sections may be employed without departing from the spirit of the present invention. Similarly, the present duckbill seal bodies 130, 132 may be constructed with an infinite number of angles, that is, with a continuous curving surface, without departing from the spirit of the present invention.

Regardless of the exact wall construction employed, the wall angle should be maintained low (for example, 30 degrees) where instruments do not ordinarily contact the seal bodies 130, 132 of the duckbill seal assembly 32 and increase to a high value (for example, 45 degrees) where instruments customarily contact the wall surface of the seal bodies 130, 132.

By orienting first and second sections 148, 150 in this manner, that is, by varying the wall angles along the extent of the seal bodies 130, 132, tear resistance is improved without adjusting the overall height of the duckbill seal assembly 32. By providing a low wall angle at the position where instruments do not customarily contact the seal bodies 130, 132 the overall height of the duckbill seal assembly 32, and ultimately the trocar assembly 10, may be minimized, while accommodating proper seal function. The application of a high wall angle at the location where instruments customarily contact the seal bodies 130, 132 minimizes normal forces contacting the duckbill seal assembly 32 and consequently minimizes the potential for tearing of the duckbill seal assembly 32.

As discussed above, the height of the trocar sleeve 44 is a critical issue due to its impact on ergonomics. At the same time, the duckbill drag, durability, and sealing functions must all be balanced with the need for minimized trocar sleeve 44 height.

In order to provide a superior design in accordance with the present duckbill seal assembly 32, the height of the duckbill seal assembly 32 is minimized by using two wall angles. The wall angle along the first section 148 is shallow to minimize the height. At a given critical diameter, the wall angle becomes steeper at the second section 150. This steeper wall provides a lower attack angle with respect to an inserted instrument to maximize durability. At the same time, the sealing function is improved due to the greater closure forces from the abdominal gas pressures acting on the second section with the lower attack angle due to the steeper wall, as compared with the angle of the first section 148.

Despite the advantages offered by the multi-angle design, forces between the duckbill seal assembly 32 and the instrument must still be further minimized. This is accommodated through wall thickness, rib geometry and surface coating adjustment. The lower drag forces are desirable to reduce the effort required by a surgeon when inserting or withdrawing instruments from a trocar sleeve 44. Reducing the effort required is desirable for permitting one-handed insertion or withdrawal of an instrument. This also reduces the possibility of a trocar sleeve 44 being pulled out of a patient into which the trocar assembly 10 was inserted.

As discussed, and while angles of 30 and 45 degrees are utilized in accordance with a preferred embodiment, as larger diameter instruments are required, larger diameter duckbill seal assemblies 32 will also be required. As space is usually at a premium in valve applications, especially for duckbill seal assemblies 32 when used in trocar assemblies, minimal height is very desirable. Seal durability is paramount so an angle of forty-five degrees is used to minimize tearing of the seal bodies 130, 132 while inserting or withdrawing instruments.

In accordance with a preferred embodiment, the duckbill seal assembly 32 is an elastomer or a cross linked polymer such as, but not restricted to, polyisoprene or silicone.

Endoscope Lock assembly

Figure 3:
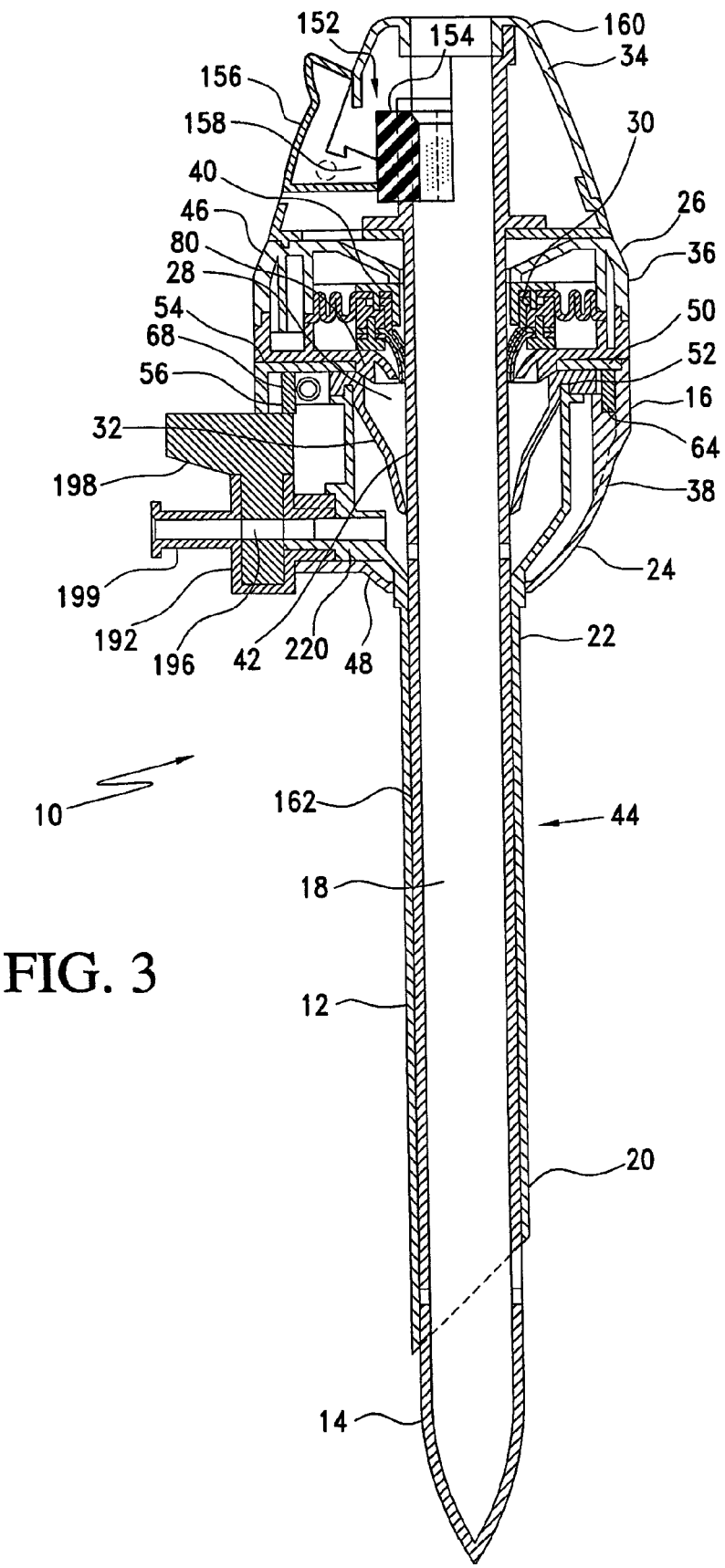
FIG. 3 is a cross sectional view of the trocar assembly shown in FIG. 1.
Figure 4:
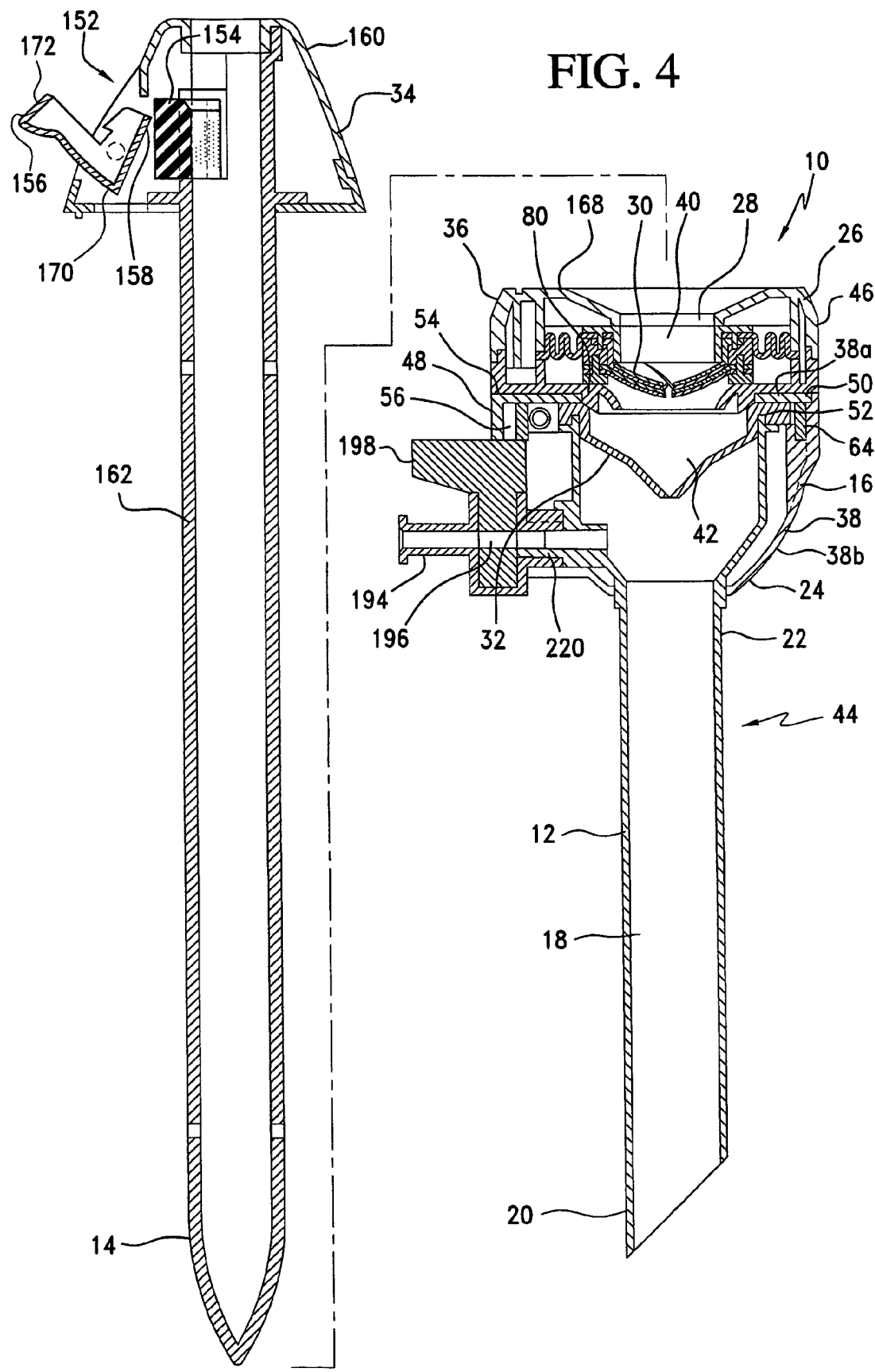
FIG. 4 is an exploded cross sectional view of the trocar assembly shown in FIG. 1.
Figure 5:
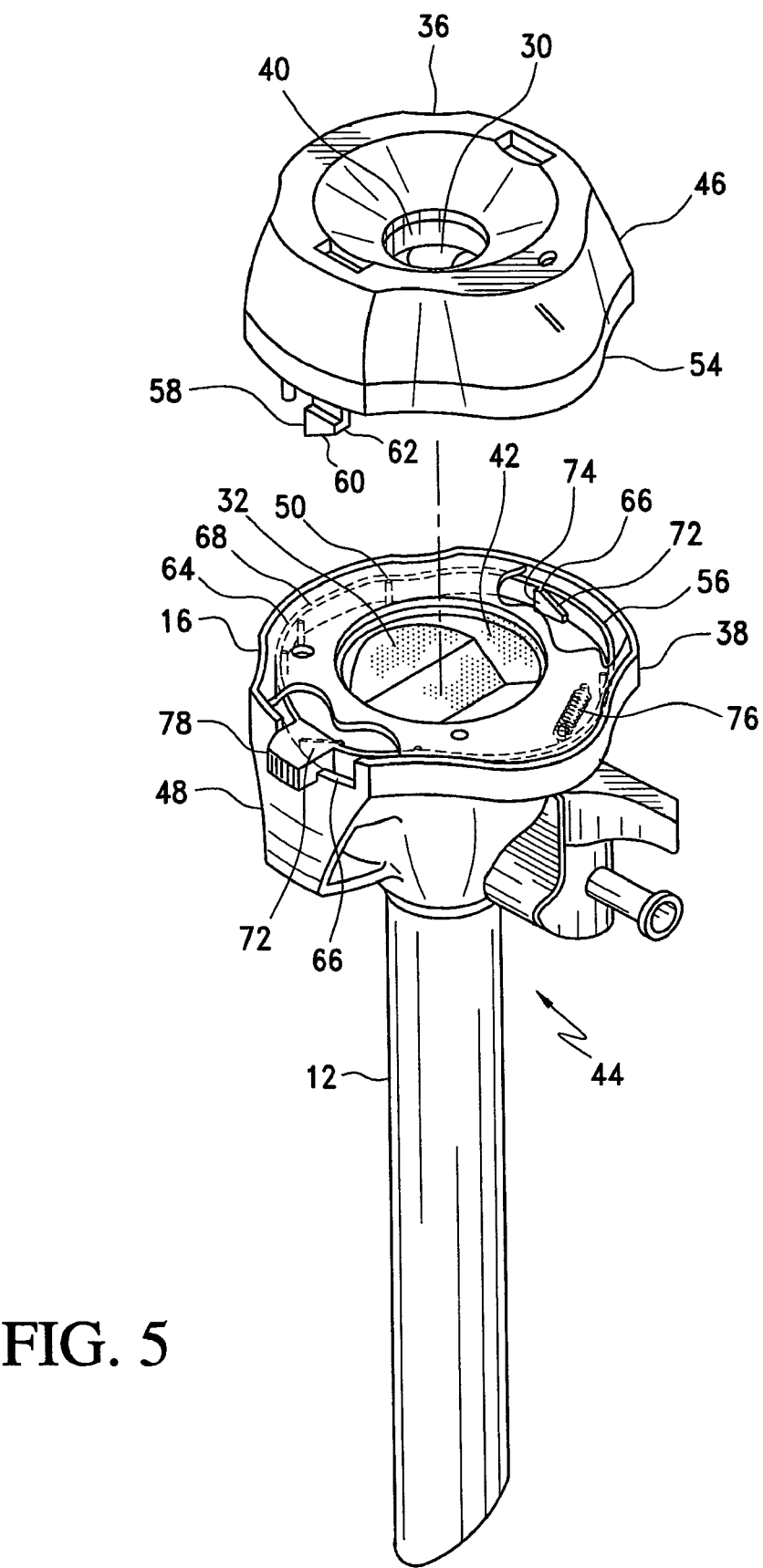
FIG. 5 is a detailed view of the rotary latch mechanism utilized in accordance with the present trocar assembly.
Figure 6:
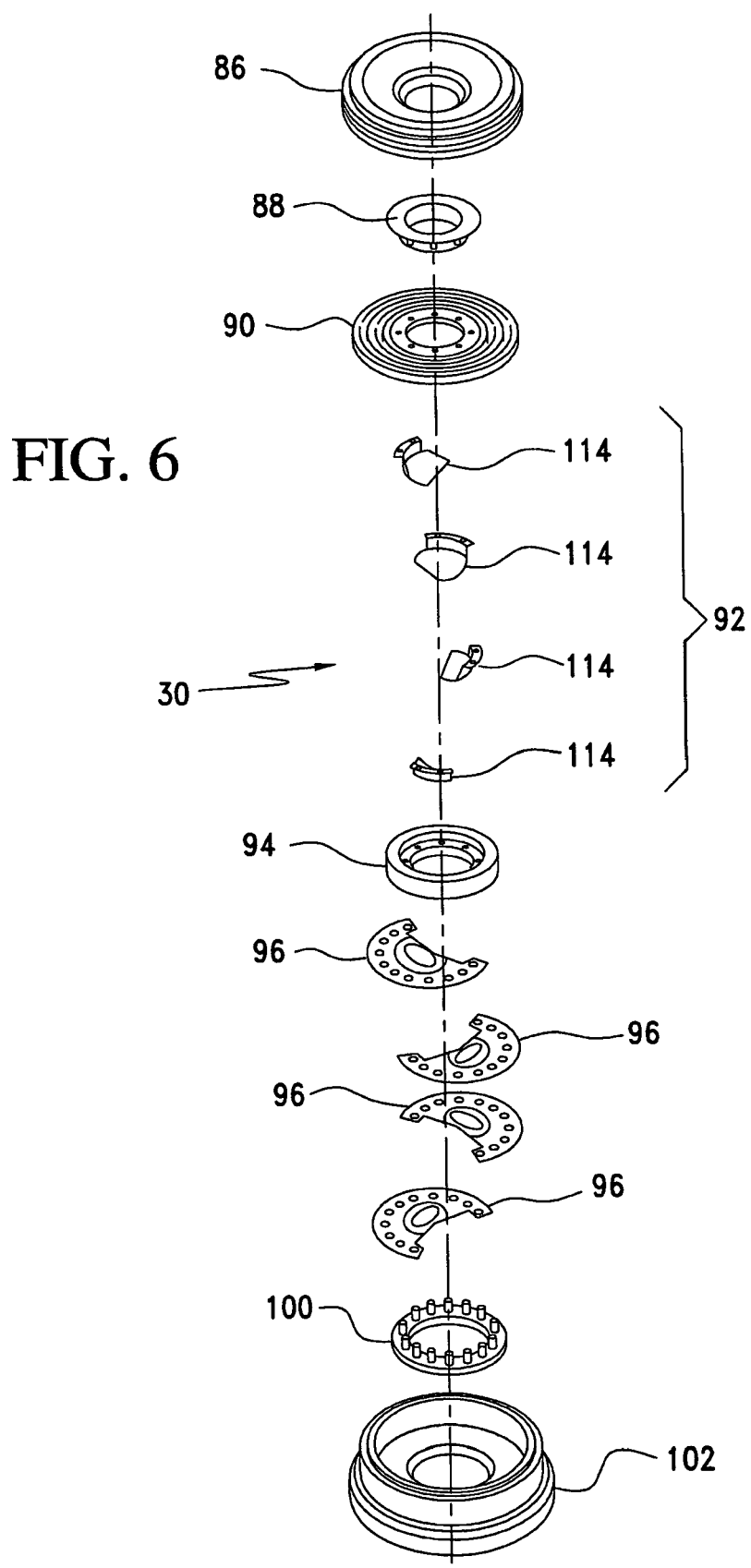
FIG. 6 is an exploded view of the proximal seal assembly in accordance with the present trocar assembly.
Figure 25:
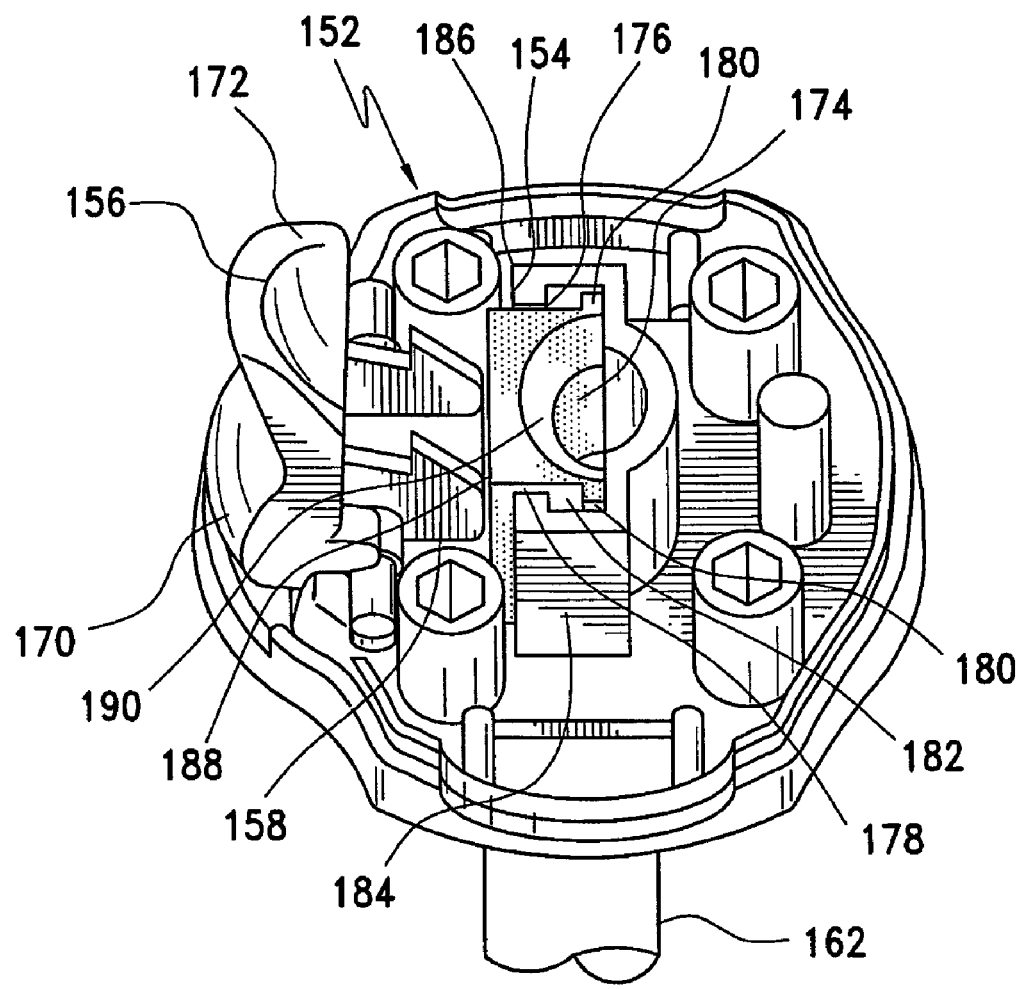
FIG. 25 is a detailed view of the endoscopic lock mechanism.

As discussed above in the Background of the Invention, it is often desirable to lock an endoscope in position relative to a trocar assembly 10, in particular, an obturator 14. As such an endoscope lock assembly 152 is provide in accordance with the present invention and is shown in FIGS. 3, 4 and 25. The endoscope lock assembly 152 generally includes a cam mechanism that retains an endoscope within a trocar sleeve 44 and/or obturator 14 during insertion of trocar assembly 10. The mechanism uses a cam to compress an elastomeric block 154 against the endoscope. The elastomeric block 154 then grips the endoscope tightly to prevent undesired motion of the endoscope as the surgeon is visualizing the tissue layers during the trocar assembly insertion. The cam mechanism provides for the ability to retain the endoscope while resisting both torque and axial loads, provides for acceptable endoscope retention after repeated throws of the cam lever 156, provides low ergonomic forces to actuate the cam lever 156, provides for compatibility with a wide range of endoscope sizes, facilitates intuitive use and has a long term shelf life stability.

The cam mechanism that retains the endoscope within a trocar assembly 10 uses a cam surface 158 to compress the elastomeric block 154 against the endoscope. The elastomeric block 154 then grips the endoscope tightly to prevent undesired motion of the endoscope as the surgeon is visualizing the tissue layers during the trocar assembly insertion.

The lock assembly 152 includes a housing 160 having a tube 162 extending therefrom. The tube 162 is aligned with an aperture extending therethrough. The tube is formed with a sharp tip and may be utilized as an obturator in accordance with the present invention. The tube 162 and the aperture are shaped and dimensioned for the extension of an endoscope therethrough. In addition, the tube 162 is shaped and dimensioned to extend through the trocar cannula 12 such that the lock assembly 152, including the tube 162, may be selectively secured to the trocar sleeve 44 for the use of an endoscope.

Attachment of the lock assembly 152 to the trocar first housing member 36 is achieved via mating latches 164, 166 formed on both the underside of the lock assembly housing 160 and the upper surface 168 of the first housing member 36. The latches 164, 166 permit selective attachment and release of the lock assembly 152 to the trocar housing 16. While a specific latching structure is disclosed in accordance with a preferred embodiment of the present invention, other latching structures may be utilized without departing from the spirit of the present invention.

The lock assembly housing 160 includes a camming based locking mechanism. The locking mechanism is composed of a cam lever 156 and an elastomeric block 154. The cam lever 156 includes a first end 170 that is pivotally secured to the housing 160 and a free second end 172 that is adapted for user actuation. In practice, the cam lever 156 may be freely moved between a locking position in which the cam lever 156 is rotated inwardly and a release position in which the cam lever 156 is rotated outwardly.

Camming action in accordance with the present invention is provided by a camming surface 158 adjacent the first end 170 of the cam lever 156. The camming surface 158 is shaped and dimensioned to engage the elastomeric block 154 for selectively locking an endoscope within the lock assembly 152. With regard to the elastometic block 154, it is housed within the body of the lock assembly housing 160 and includes a forward concave wall 174 shaped and dimensioned for engaging an endoscope passing through the housing aperture. The elastomeric block 154 further includes first and second side walls 176, 178, wherein each side wall 176, 178 includes a notch 180 for engagement with a channel 182 formed within the body of the housing 160. The channel 182 and notch 180 interact to allow lateral movement of the elastomeric block 154 in a manner that is described below in greater detail. The housing 160 further includes upper and lower retaining members 184, 186 for securely preventing upward or downward motion of the elastomeric block 154 within the housing 160. Finally, the elastometic block 154 includes a rear wall 188 opposite the forward concave wall 174. The rear wall 188 is shaped and dimensioned for engagement with the camming surface 158 of the cam lever 156.

The elastometic block 154 and the camming surface 158 are shaped to eliminate forceful contact, and in particular eliminate any contact, between the elastomeric block 154 and the camming surface 158 until such a time that an endoscope is positioned with the aperture of the lock assembly housing 160. As will be described below in greater detail, when an endoscope if placed within the aperture of the lock assembly housing 160, the elastomeric block 154 is moved toward the cam lever 156 to such a degree that the elastometic block 154 comes into proximity of the camming surface 158 for locking of the endoscope within the aperture once the cam lever is actuated.

In practice, the lock assembly 152 is used in the following manner. The elastomeric block 154 sits within the lock assembly housing 160 underneath the cam lever 156, which may be either open or closed during long-term storage. The elastomeric block is purposefully not in contact with the cam lever 156 at this point to avoid any loads on the elastomeric block 154 that could affect the lock assembly's 152 performance after long-term storage. The surgeon then opens the cam lever 156 if it was originally closed. An endoscope is inserted into the lock assembly 154. The endoscope hits a chamfered surface 190 on the concave wall 174 of the elastomeric block 154. This lifts the elastomeric block 154 upward into the proximity of the cam lever 156. The elastomeric block 154 then rests on top of the endoscope for the rest of its use. The cam lever 156 is then actuated, which compresses the compressible scope lock onto the endoscope. The compliance of the elastomeric block 154, along with its high coefficient of friction, allows the lock assembly 152 to be compatible with a wide range of endoscope sizes while minimizing ergonomic force requirements. The elastomeric block 154 is then constrained from excessive sideways or axial motion by surrounding components 182, 184, 186 that limit its motion as axial and torsional loads are applied to the endoscope. This constraint, along with an over-center cam design, prevents the cam lever from accidentally unlocking by itself by accident. After the trocar assembly 10 has been inserted into the patient, the cam lever 156 is then opened and the endoscope is removed. The elastomeric block 154 then returns to its original position in the lock assembly 152 if the surgeon wishes to reinsert the endoscope at a later time. The compliant elastomeric block 154 has sufficient rigidity to return to its original shape after the load from the cam lever 156 has been removed, thus providing acceptable endoscope retention force over the course of multiple lever actuations.

Trocar Sleeve and Stop-Cock Valve Construction

As mentioned above, the trocar sleeve 44 is composed of a trocar housing 16 and a trocar cannula 12 extending from the trocar housing 16. The trocar assembly 10 also includes a stop-cock valve 192 for allowing and preventing the passage of an insufflation fluid, e.g. carbon dioxide, through flexible tubing into a portion of the trocar housing 16 and the trocar cannula 12.

With reference to the figures, the trocar cannula 12 and the trocar housing 16 are mechanically interfitted to form the trocar sleeve 44. At least a portion of the trocar cannula 12 sits within a second housing member base 38*b* of the second housing member 38 with a second housing member cover 38*a* sitting over the trocar cannula 12 for securing the at least a portion of the trocar cannula 12 within the second housing member base 38*b*.

The trocar cannula 12 is sized so that when the trocar obturator 14 extends completely through it and beyond, insufflation fluid, which passes through the stop-cock valve 192 and the trocar housing 16, can pass through an annular opening created between the trocar cannula 12 and the trocar obturator 14 by the slightly greater size of the internal diameter of the trocar cannula 12 in relation to the outer diameter of the hollow shaft of the trocar obturator 14.

The present invention provides a mechanism for mechanically assembling the trocar cannula 12, trocar housing 16 and stop-cock valve 192 without the need for adhesive and/or curing techniques. In particular, the second housing member 38 of the trocar housing 16, trocar cannula 12 and stop-cock valve 192 are formed as separate components that may be assembled in a convenient and reliable manner.

More particularly, and with reference to FIGS. 17, 18, 19 and 20, a preferred embodiment of the mechanically assembled trocar sleeve 44 is disclosed. The trocar sleeve 44, when, fully assembled, comprises a stop-cock valve 192, a second housing member 38 composed of a second housing member cover 38a and a second housing member base 38b, and a trocar cannula 12. The various components of the trocar sleeve 44 are mechanically assembled by interfitting the components in a manner that is described below in greater detail. Briefly, the trocar cannula 12 fits within the second housing member base 38b with the stop-cock valve 192 positioned therebetween. The second housing member cover 38a fits over the stop-cock valve 192, second housing member base 38b and trocar cannula 12 to retain the various components together and provided a surface upon which the first housing member 36 may be selectively mounted.

With regard to the specific components making up the trocar sleeve 44, and in accordance with a preferred embodiment of the present invention, the stop-cock valve 192 includes alignment wings 194, a flow opening 196, and a valve lever 198. The valve lever 198 includes a stop latch 200. The second housing member cover 38a includes a hexagonal bore 202, a cover rim 204, and a second housing member cover seal 206. The second housing member base 38b includes friction posts 208, vanes 210, a housing rim 212, a clearance 214 for the stop-cock valve 192 and alignment wings 194. The second housing member base 38b further includes alignment ribs 216 and a latching face 218. The trocar cannula 12 includes an inlet nipple 220, alignment tabs 222, and a housing seal 224.

In practice, the stop-cock valve 192 is inserted into the clearance 214 of the second housing member base 38b. The trocar cannula 12 inserts through the opening of the second housing member base 38b. The alignment tabs 222 abut the vanes 210 securing the trocar cannula 12 in a desired orientation with respect to the second housing member base 38b once the trocar cannula 12 is inserted into the second housing member base 38b.

The cover rim 204 mates with the housing rim 212. The cover rim 204 also serves to hold the valve lever 198 on the stop-cock valve 192 as well as hold the stop-cock valve 192 with the valve lever 198 in position.

The valve lever 198, in a maximum flow allowance position, i.e., fully open, has the stop latch 200 abut onto the latching face 218 of the second housing member base 38b. This means an operator of the valve lever 198 can sense when the valve lever 198 is in a fully open position by abutting latch face 218 and the valve lever 198 stays in the fully open position. The operator does not have to guess that the valve lever 198 is in the fully open position, and the valve lever 198 stays in the fully open position.

The construction of the trocar assembly 44 eliminates the need for adhesives to join the stop-cock valve 192 and the second housing member cover 38a, and the second housing member base 38b and the trocar cannula 12. This is an advantage over prior art.

Referring to FIGS. 21 and 22, an alternate trocar sleeve 44' is disclosed. In accordance with this alternate embodiment, the trocar sleeve 44' includes a stop-cock valve 192', a second housing member cover 38a', and a second housing member base 38b'. The trocar sleeve 44' also includes a trocar cannula 12' which is substantially similar to the trocar cannula 12 disclosed in accordance with the prior embodiment.

The stop-cock valve 192' comprises a valve tube taper lock extension 226', a friction post 228' and a valve lever 198'. The second housing member base 38b ' comprises an extension clearance 230', and a friction post hexagonal bore 232'.

The valve tube taper lock extension 226' of the stop-cock valve 192' locks into the extension clearance 230' of the second housing member base 38b'. The friction post 228' of the stop-cock valve 192' fits into the friction post hexagonal bore 230' of the second housing member base 38b', securing the vertical alignment of the stop-cock valve 192' with respect to the second housing member base 38b'.

Figure 23:
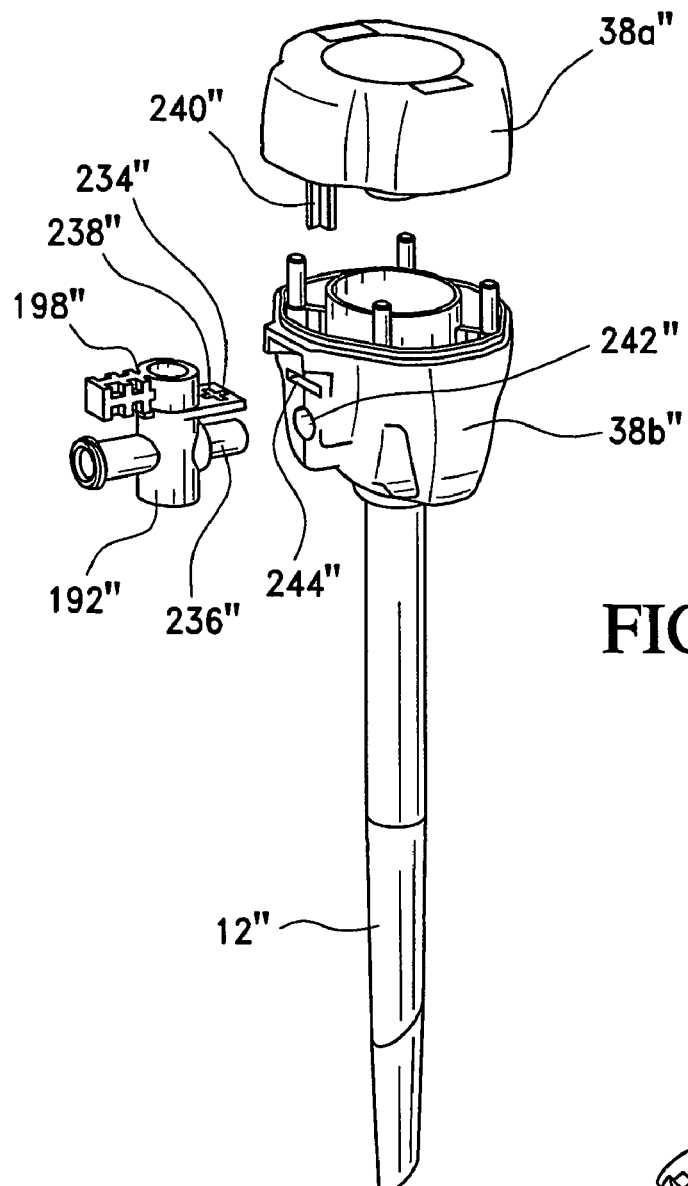
FIGS. 23 and 24 are exploded views of a further embodiment of the trocar sleeve.
Figure 24:
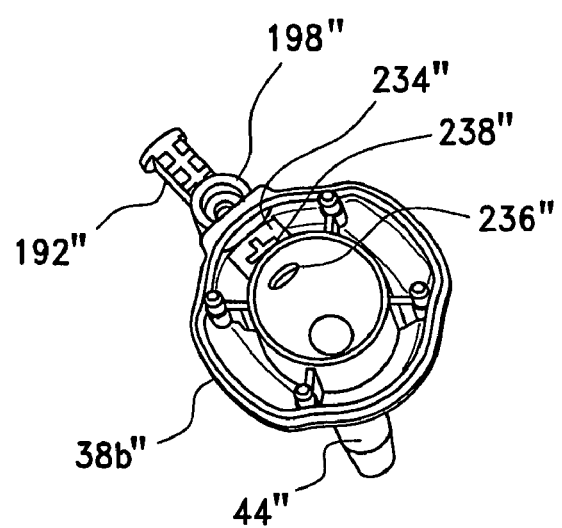

Referring to FIGS. 23 and 24, a further embodiment is disclosed. In accordance with this further embodiment, the trocar sleeve 44" comprises a second housing member cover 38a", a second housing member base 38b", and a stop-cock valve 192". The trocar sleeve 44" also includes a trocar cannula 12" which is substantially similar to the trocar cannula 12 disclosed in accordance with the prior embodiment.

The stop-cock valve 192" comprises a locking groove boss 234", a valve tube extension 236", and a locking groove 238". In addition, the second housing member cover 38a " includes a locking tongue 240". The second housing member base 38b " also comprises a valve tube extension aperture 242" and a boss clearance 244". The valve tube extension 236" of the stop-cock valve 192" inserts and locks, by friction fit or taperlock, into the valve tube extension aperture 242" of the second housing member base 38b". The locking groove boss 234" of the stop-cock valve 192" locks into the boss clearance 244". This serves to assist in securing the stop-cock valve 192" in the second housing member base 38b".

As mentioned above, the stop-cock valve 192 is mechanically coupled to the trocar sleeve 44 via tapered surfaces shaped and dimensioned for frictional engagement. As such, the outlet tube 250 of the stop-cock valve 192 is formed with a tapered lock surface along the exterior of its distal end. Similarly, the trocar cannula 12 is formed with an inlet nipple 220, adapted for secure coupling with the tapered lock surface of the outlet tube 250 of the stop-cock valve 192. The tapered lock mechanical feature includes a self holding 2.0 degrees +−1.0 degrees angle, which is firmly seated into the trocar housing inlet nipple 220. The result of this mechanical connection is considerable frictional resistance to rotational and linear pull out forces.

The mechanical lock discussed above may be enhanced by the provision of a dual redundancy feature. For example, the taper lock feature may be provided with a post and hex socket interlock, tongue and groove interlock and/or a snap fit interlock.

In addition, and in accordance with the embodiment described above with reference to FIG. 18, rotation of the stop-cock valve 192 is minimized by the inclusion of a retaining pin 204 located on the second housing member cover 38a that extends downwardly into the aperture 256 formed in the top of the valve lever 198. The retaining pin 204 stabilizes the stop-cock valve 192 and prevents rotation as the valve lever 198 of the stop-cock valve 192 is actuated.

As mentioned above, the trocar sleeve includes a stop-cock valve 192. The stop-cock valve 192 is mounted within a recess formed in the trocar sleeve 44. As such, the stop-cock valve 192 recessed within the outer surface of the second housing member base 38b, and ultimately the trocar housing 16. The valve lever 198 is further positioned above the body of the stop-cock valve 192; that is, the valve lever 198 used in actuating the stop-cock valve 192 is positioned on the top surface of the stop-cock valve 192 instead of underneath as with trocar assemblies currently in the marketplace. By positioning the valve lever 198 above the recessed stop-cock valve 192, the present trocar assembly 10 provides for the removal of the stop-cock valve 192 from a potentially obstructing view while simultaneously placing the valve lever 198 in a highly accessible position.

Several advantages are achieved by recessing the stop-cock valve 192 within the body of the trocar sleeve 44. First, this orientation minimizes the obstructions caused by users gripping the stop-cock valve 192 of the trocar assembly 10 for insertion. A more comfortable grip is, therefore, provided, as the stop-cock valve 192 no longer protrudes from the surface of the trocar housing 16. The present low profile stop-cock valve 192 structure further helps to prevent compromising desired hand positions. The present stop-cock valve 192 orientation also helps to prevent accidental manipulation during procedures. Accidental manipulation by movement of the trocar sleeve 44 into contact with a patient is a common occurrence that results in desufflation of the body cavity and can lead to frustrating and even dangerous situations when the medical professional's field of view is compromised.

The advantages are further enhanced by forming the valve lever 198 with a curved surface substantially conforming to that of the trocar housing 16. In addition, the longitudinal axis along the handle portion of the valve lever 198 is offset from the pivot point about which the valve lever 198 rotates so as to enhance recessing of the stop-cock valve 192. Controlled rotation of the valve lever 198 of the stop-cock valve 192 is achieved through the positioning of the stop-cock valve 192 within a recess formed in the trocar sleeve 44, more specifically, the trocar housing 16. Specifically, and with reference to FIGS. 17, 18, 19 and 20, the valve lever 198 of the stop-cock valve 192 includes a stop latch 200 located on the valve 198 which provides tactile feedback as to when the valve lever 198 is in the open position, i.e., the through holes located on the valve lever 198 and valve body 199 are aligned. The design feature resembles a cantilever beam located on the end of the valve lever 198 opposite the user end.

As the valve lever 198 is rotated from the closed position to the open position within the trocar assembly 10, the cantilever rotational stop latch 200 contacts the trocar housing 16 providing tactile feedback that the valve lever 198 is in the fully opened position. In the fully opened position, the valve lever 198 and valve body 199 through holes are aligned allowing for optimal $CO_2$ flow.

The cantilever rotational stop latch 200 feature provides the surgeon with tactile feedback to ensure that the stop-cock valve 192 is in the open position. This will provide the optimal flow of $CO_2$ flow throughout the surgical case.

As those skilled in the art will appreciate, control of the valve lever 198 via the cantilever rotational stop latch 200 helps in alignment of the stop-cock valve 192 through hole 196. Misalignment of through holes 196 is commonly caused by lack of tactile feedback to the surgeon that the valve lever 198 is in the fully opened position.

In addition, a strengthening gusset 264 is located on the backside of the cantilever rotational stop latch 260 to prevent over-rotation of the valve lever 198 by bending the valve lever 198. This can be seen in FIGS. 17 and 18. Over-rotation would create misalignment of the through holes.

As those skilled in the art will certainly appreciate, the design described above offers many advantages over prior art assemblies. The separate trocar cannula 12 design described above provides for interchangeable outer housing capabilities. As such, the industrial design outside shape can be readily changed and updated without changing the internal structure of the trocar sleeve. In addition, assembly of the trocar cannula 12 to the trocar housing 16 joint system eliminates the need for ultrasonic welding. The present assembly method makes the device stronger by molding the trocar cannula 12 in one part. As those skilled in the art will certainly appreciate, prior designs utilized ultrasonic weld joints to assemble the trocar cannula 12 to the trocar housing 16. The present assembly structure eliminates the use of such joints and, therefore, provides no opportunity for failure of the ultrasonic weld joints.

In addition, the trocar housing 16 is provided with crush ribs 266 along its internal surface. These crush ribs 266 center the trocar cannula 12 within the trocar housing 16. They also take up small variations in tolerances making the size of the trocar cannula 12 during manufacture less important and allowing for inherent variations during the molding process.

The crush ribs 266 further prevent rotation of the trocar cannula 12 within the trocar housing 16. This is achieved as the crush ribs 266 extend into the sides of the trocar cannula 12 thereby preventing relative rotation between the trocar cannula 12 and the trocar housing 16.

Since the trocar housing 16 and trocar cannula 12 are rather simple in construction, the molding process is simplified by eliminating excessive core details on the injection mold tool. In addition, assembly of the system is easy as compared to prior designs as all of the components making up the sleeve assembly can be assembled in a top down manner.

As to the stop-cock valve 192, the taper lock with dual redundant locking features helps to prevent the stop-cock valve 192 from falling off the trocar sleeve 44. In addition, the taper lock provides an airtight assembly without the use of adhesive or welding. In addition, the stop-cock valve 192 is provided with various lock surfaces preventing rotation of the stop-cock valve 192, for example, post and socket, tongue and groove, wings on ribs, etc. In addition to the taper lock features, the wings are trapped behind the trocar housing 16, eliminating the possibility for removal of the stop-cock valve 192 from the trocar sleeve 44. In addition, crush ribs 266 are utilized in holding the wings tight onto the trocar cannula 12. Finally, the low profile stop-cock valve 192 structure with a valve lever 198 positioned above the stop-cock valve 192 allows for alignment of the stop-cock valve 192 to provide optimal air flow and offers users a tactile feedback for optimizing alignment.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A seal assembly for use in conjunction with a trocar assembly, the seal assembly comprising: a seal body adapted for sealing about an instrument inserted through the trocar assembly; a protector adjacent the seal body for protecting the seal body from instruments passing through the seal body, the protector comprising a plurality of flexible, elastomeric protector segments woven together in a non-planar arrangement, wherein each protector segment includes an integrally formed peripheral edge, which is substantially round and is secured directly to a housing of the trocar assembly, a flexible, elastomeric protector member, and a support wall connecting the peripheral edge to the protector member, each protector segment further includes a first section and a second section on opposite sides of the protector segment, wherein the protector segments are assembled in an overlapping woven arrangement to provide a complete protector with the first section lying over the second section of an adjacent protector segment;

and wherein the peripheral edge, when viewed from above, defines an arc extending between a first lateral edge of the peripheral edge and a second lateral edge of the peripheral edge, the support wall, when viewed from above, defines an arc extending between a first lateral edge of the support wall and a second lateral edge of the support wall, and wherein the protector member, when viewed from above, defines an arc extending between a first lateral edge of the protector member and a second lateral edge of the protector member, and wherein the arc defined by the protector member is larger than the arc defined by either the peripheral edge or the support wall.

2. The seal assembly according to claim 1, wherein the protector segments overlap such that as an instrument is inserted into the protector the protector segments spread, exposing additional portions of the protector segments positioned behind adjacent protector segments.

3. The seal assembly according to claim 1, wherein four protector segments are assembled to create the protector.

4. The seal assembly according to claim 1, wherein at least two protector segments are assembled to create the protector.

5. The seal assembly according to claim 1, wherein each of the protector segments is substantially semi-circular.

6. The seal assembly according to claim 1, wherein the arc defined by the protector member is and the arc defined by the support wall and the peripheral edge is approximately 120 degrees.

7. The seal assembly according to claim 1, wherein the peripheral edge of each protector segment includes a series of apertures which function as a means of attachment for the protector segments.

8. The seal assembly according to claim 1, wherein a slot is formed within the peripheral edge of each of the protector segments to reduce instrument insertion forces.

9. The seal assembly according to claim 1, wherein the protector includes four individual protector segments combined in a woven arrangement by placing a first section of a first protector segment upon a second section of a second protector segment, placing a first section of the second protector segment upon a second section of a third protector segment, placing a first section of the third protector segment upon a second section of a fourth protector segment and placing a first section of the fourth protector segment upon the second section of a first protector segment.

10. The seal assembly according to claim 9, wherein each protector segment is substantially cone shaped such that the resulting protector is cone shaped.

11. The seal assembly according to claim 1, wherein the protector contacts the seal body.

12. A trocar assembly, comprising: a trocar cannula including a proximal end and distal end; and a trocar housing coupled to the proximal end of the trocar cannula for receiving and guiding an obturator through the trocar cannula, the trocar housing includes an open proximal end portion defining an opening provided with a proximal seal assembly and a distal seal assembly; the proximal seal assembly including a seal body adapted for sealing about an instrument inserted through the trocar assembly, a protector adjacent the seal body for protecting the seal body from instruments passing through the seal body, and a support wall connecting a peripheral edge to the protector member, the protector comprising a plurality of flexible, elastomeric protector segments woven together in a non-planar arrangement, wherein each protector segment includes an integrally formed peripheral edge which is substantially round and is secured directly to the trocar housing, and a flexible, elastomeric protector member, each protector segment further includes a first section and a second section on opposite sides of the protector segment, wherein the protector segments are assembled in an overlapping woven arrangement to provide a complete protector with the first section lying over the second section of an adjacent protector segment;

and wherein the peripheral edge, when viewed from above, defines an arc extending between a first lateral edge of the peripheral edge and a second lateral edge of the peripheral edge, the support wall, when viewed from above, defines an arc extending between a first lateral edge of the support wall and a second lateral edge of the support wall, and wherein the protector member, when viewed from above, defines an arc extending between a first lateral edge of the protector member and a second lateral edge of the protector member, and wherein the arc defined by the protector member is larger than the arc defined by either the peripheral edge or the support wall.

13. The trocar assembly according to claim 12, wherein the protector segments overlap such that as an instrument is inserted into the protector the protector segments spread, exposing additional portions of the protector segments positioned behind adjacent protector segments.

14. The trocar assembly according to claim 12, wherein four protector segments are assembled to create the protector.

15. The trocar assembly according to claim 12, wherein at least two protector segments are assembled to create the protector.

16. The trocar assembly according to claim 12, wherein each of the protector segments is substantially semi-circular.

17. The trocar assembly according to claim 12, wherein the arc defined by the protector member is and the arc defined by the support wall and the peripheral edge is approximately 120 degrees.

18. The trocar assembly according to claim 12, wherein the peripheral edge of each protector segment includes a series of apertures which function as a means of attachment for the protector segments.

19. The trocar assembly according to claim 12, wherein a slot is formed within the peripheral edge of the each protector segment to reduce instrument insertion forces.

20. The trocar assembly according to claim 12, wherein the protector includes four individual protector segments combined in a woven arrangement by placing a first section of a first protector segment upon a second section of a second protector segment, placing a first section of the second protector segment upon a second section of a third protector segment, placing a first section of the third protector segment upon a second section of a fourth protector segment and placing a first section of the fourth protector segment upon the second section of a first protector segment.

21. The trocar assembly according to claim 20, wherein each protector segment is substantially cone shaped such that the resulting protector is cone shaped.

22. The trocar assembly according to claim 12, wherein the protector contacts the seal body.

23. The seal assembly according to claim 1, wherein the peripheral edge includes a central slot.

24. The trocar assembly according to claim 12, wherein the peripheral edge includes a central slot.

* * * * *